US012640084B2

(12) United States Patent (10) Patent No.: US 12,640,084 B2

Kim et al. (45) Date of Patent: May 26, 2026

(54) ELECTRONIC DEVICE AND METHOD OF DRIVING THE SAME

(71) Applicant: SAMSUNG DISPLAY CO., LTD., Yongin-si (KR)

(72) Inventors: Chul Kim, Yongin-si (KR); Dong Wook Yang, Yongin-si (KR)

(73) Assignee: SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 18/524,949

(22) Filed: Nov. 30, 2023

(65) Prior Publication Data

US 2024/0296785 A1 Sep. 5, 2024

(30) Foreign Application Priority Data

Mar. 3, 2023 (KR) ........................ 10-2023-0028609

(51) Int. Cl.
 *G09G 3/32* (2016.01)
 *A61B 5/02* (2006.01)
(52) U.S. Cl.
 CPC ................. *G09G 3/32* (2013.01); *A61B 5/02* (2013.01); *G09G 2320/0626* (2013.01); *G09G 2340/0407* (2013.01)
(58) Field of Classification Search
 None
 See application file for complete search history.

(56) References Cited

U.S. PATENT DOCUMENTS

| | | | |
|---|---|---|---|
| 10,083,674 B2 | 9/2018 | Gu et al. | |
| 10,398,324 B2 | 9/2019 | Mukkamala et al. | |

| | | | |
|---|---|---|---|
| 11,106,309 B1 * | 8/2021 | Trapero Martin | . G06V 40/1318 |
| 11,179,047 B2 | 11/2021 | Mukkamala et al. | |
| 11,430,360 B2 | 8/2022 | Lee et al. | |

(Continued)

FOREIGN PATENT DOCUMENTS

| | | |
|---|---|---|
| KR | 10-2021-0126802 | 10/2021 |
| KR | 10-2022-0021083 | 2/2022 |
| KR | 10-2022-0056313 | 5/2022 |

OTHER PUBLICATIONS

Khan, et al., "Organic Multi-Channel Optoelectronic Sensors for Wearable Health Monitoring", IEEE Access, vol. 7, Sep. 6, 2019, pp. 128114-128124.

(Continued)

*Primary Examiner* — Andre L Matthews
(74) *Attorney, Agent, or Firm* — F. CHAU & ASSOCIATES, LLC

(57) ABSTRACT

An electronic device and a method of driving the electronic device. The electronic device may include: a display panel including a display area, with photo sensors and pixels disposed in the display area; a panel driving circuit configured to cause pixels located in a light emitting area of the display area to emit light; a sensing circuit configured to sense signals of the photo sensors located in a light receiving area of the display area; a memory configured to store at least one application; and a processor configured to vary a setting of at least one of the light emitting area and the light receiving area depending on the application executed with reference to the memory. The electronic device and the method of driving the electronic device may provide a biometric authentication function and a biometric signal measuring function.

24 Claims, 23 Drawing Sheets

<MODE 2>

210
NA
AA
AREA 2
AREA 3

(56)  References Cited

U.S. PATENT DOCUMENTS

| | | | |
|---|---|---|---|
| 11,665,439 | B2 | 5/2023 | Kim et al. |
| 2010/0134531 | A1 | 6/2010 | Kinugasa |
| 2014/0152633 | A1 | 6/2014 | Park et al. |
| 2018/0089491 | A1 | 3/2018 | Kim et al. |
| 2018/0089494 | A1 | 3/2018 | Zhu et al. |
| 2018/0173923 | A1 | 6/2018 | Lee et al. |
| 2018/0196931 | A1 | 7/2018 | Cho et al. |
| 2019/0130156 | A1 | 5/2019 | Yun et al. |
| 2019/0362672 | A1 | 11/2019 | Cui et al. |
| 2020/0175249 | A1 | 6/2020 | Kim et al. |
| 2020/0279086 | A1* | 9/2020 | Wang ................. G06V 40/1318 |
| 2021/0064159 | A1 | 3/2021 | Yeke Yazdandoost et al. |
| 2021/0319198 | A1 | 10/2021 | Seomoon et al. |
| 2021/0327948 | A1 | 10/2021 | Liu et al. |
| 2021/0327971 | A1 | 10/2021 | Hyun et al. |
| 2022/0047170 | A1 | 2/2022 | Seomoon et al. |
| 2022/0075979 | A1* | 3/2022 | Han ................... G06V 40/1318 |
| 2023/0205347 | A1 | 6/2023 | Joo et al. |
| 2023/0316996 | A1 | 10/2023 | Ozbas et al. |
| 2024/0295765 | A1 | 9/2024 | Kim et al. |
| 2024/0313011 | A1 | 9/2024 | Lu et al. |

OTHER PUBLICATIONS

Taisuke, et al., "OLED display incorporating organic photodiodes for fingerprint imaging", Journal of the Society, vol. 27, Issue6, Apr. 15, 2019, DOI: 10.1002/jsid.786, pp. 361-371.
Office Action dated Sep. 19, 2024 in U.S. Appl. No. 18/407,449.
Office Action dated Apr. 24, 2025 in related U.S. Appl. No. 18/407,449.

* cited by examiner

PXR[1]

PXR[2]

PXR[i]

PXR[m-1]

PXR[m]

FIG. 7

<MODE 2>

ELECTRONIC DEVICE AND METHOD OF DRIVING THE SAME

CROSS-REFERENCE TO RELATED APPLICATION

The present application claims priority to Korean patent application number 10-2023-0028609 filed on Mar. 3, 2023, the entire disclosure of which is incorporated herein by reference in its entirety.

TECHNICAL FIELD

Various embodiments of the present disclosure relate to an electronic device and a method of driving the electronic device, and more particularly to an electronic device including a display device, a biometric authentication function and a biometric signal measuring function.

DESCRIPTION OF RELATED ART

With the development of information technology, electronic devices (e.g., mobile devices) have been developed to provide various functions, including a function of displaying images through display devices, to users of the electronic devices.

For example, an electronic device may provide a biometric authentication function with a high level of security using inherent biometric information (e.g., a fingerprint or the like) of a user.

Recently, to make it possible for an electronic device to assist a medical apparatus and help the user manage his/her health, various types of software which can be executed in an electronic device have been developed.

It is desirable to develop an electronic device capable of continuously generating and analyzing data (e.g., a user's biometric signals) pertaining to a user's health through development of software or other improvements of the display device.

SUMMARY

Various embodiments of the present disclosure are directed to an electronic device capable of providing a biometric authentication function and a biometric signal measuring function, and a method of driving the electronic device.

Various embodiments of the present disclosure are directed to an electronic device capable of providing a biometric authentication function and a biometric signal measuring function, with a display device having a relatively simple configuration, and a method of driving the electronic device.

Various embodiments of the present disclosure are directed to an electronic device and a method of driving the electronic device, in which a sensing resolution is controlled to vary depending on a selected mode so that a biometric authentication function with a high level of security and a biometric signal measuring function having an improved accuracy can be provided.

An embodiment of the present disclosure may provide an electronic device including: a display panel including a display area, with a plurality of photo sensors and plurality of pixels disposed in the display area; a panel driving circuit configured to cause first pixels of the plurality of pixels, which are located in a light emitting area of the display area, to emit light; a sensing circuit configured to sense signals from first photo sensors of the plurality of photo sensors, which are located in a light receiving area of the display area; a memory configured to store at least one application; and a processor configured to vary a setting of at least one of the light emitting area and the light receiving area depending on the application executed with reference to the memory.

The processor may select any one of a first mode and a second mode depending on the application executed. According to the selected first mode, a first area of the display area may be set to an emitting-sensing area including the light emitting area and the light receiving area.

The processor may select any one of a first mode and a second mode depending on the application to be executed. According to the selected second mode, a second area of the display area may be set to the light emitting area, and a third area of the display area that does not overlap the second area is set to the light receiving area.

The processor may control a sensing resolution at which the sensing circuit senses the plurality of photo sensors such that the sensing resolution is constant depending on the application executed.

The processor may be configured to select any one of a first mode and a second mode depending on the application executed, and control a sensing resolution at which the sensing circuit senses the plurality of photo sensors such that the sensing resolution varies depending on a mode selected from between the first mode and the second mode.

An embodiment of the present disclosure may provide an electronic device including: a display device including a display panel on which a plurality of photo sensors are disposed, and a readout circuit configured to sense signals from the plurality of photo sensors; and a processor configured to control a sensing resolution at which the readout circuit senses the signals from the plurality of photo sensors such that the sensing resolution varies depending on a mode selected from between a first mode and a second mode.

The electronic device may further include a memory in which reference data is stored. The processor may compare a value acquired by the readout circuit in the selected first mode with the reference data.

First software, and image data having a first sensing resolution and generated by executing the first software by the processor may be stored in the memory. The processor may execute the first software, and compare the generated image data having the first sensing resolution with the reference data.

The electronic device may further include a memory. The processor may generate image data having a second sensing resolution based on a value acquired by the readout circuit in the selected second mode. Video data having the second sensing resolution and including the image data having the second sensing resolution may be stored in the memory.

Second software, and video data having the second sensing resolution and generated by executing the second software by the processor may be stored in the memory. The processor may execute the second software, and generate biometric signal data of a user of the electronic device based on the generated video data having the second sensing resolution.

The second software may include at least one of: a blood pressure measuring module configured to measure a blood pressure of the user of the electronic device based on the video data having the second sensing resolution; a heart rate measuring module configured to measure a heart rate of the user of the electronic device based on the video data having the second sensing resolution; and an oxygen saturation measuring module configured to measure an oxygen saturation of the user of the electronic device based on the video data having the second sensing resolution.

A plurality of scan lines extending in a row direction, a first pixel row including a first photo sensor and a first pixel, a second pixel row including a second photo sensor and a second pixel, and a sensing line electrically connected to the first photo sensor and the second photo sensor may be disposed on the display panel.

The first pixel and the first photo sensor may be electrically connected to any one scan line among the plurality of scan lines. The second pixel and the second photo sensor may be electrically connected to another scan line among the plurality of scan lines.

The processor may output a control signal to allow the readout circuit to sense each of the first photo sensor and the second photo sensor in the first mode.

The processor may output a control signal to allow the readout circuit to sense both the first photo sensor and the second photo sensor in the second mode.

The readout circuit may include an integrator and a sample-and-hold circuit. The integrator may include: an operational amplifier including an input terminal electrically connected to the sensing line; and a first node electrically connected to an output terminal of the operation amplifier. The sample-and-hold circuit may include: a first capacitor element; a second capacitor element; a first switching element configured to switch electrical connection between the first node and the first capacitor element; and a second switching element configured to switch electrical connection between the first node and the second capacitor element. The processor may control a length of a period, during which the first switching element is turned on, such that the length of the period varies depending on a mode selected from between the first mode and the second mode.

The processor may output a control signal for turning on the second switching element in at least a portion of a period during which the first switching element is not turned on.

The display panel may include a display area in which a plurality of pixels including the first pixel and the second pixel and a plurality of photo sensors including the first photo sensor and the second photo sensor are disposed. The display area may include a first area in which at least one pixel among the plurality of pixels and at least one photo sensor among the plurality of photo sensors are located.

The processor, according to the selected first mode, may output image data to allow the least one pixel located in the first area to emit light, and output a control signal to sense the at least one photo sensor located in the first area.

The display area may further include a second area located in a perimeter of the first area. At least one pixel among remaining pixels and at least one photo sensor among remaining photo sensors may be located in the second area. The processor, according to the selected second mode, may output image data to allow a pixel located in any one of the first area and the second area to emit light, and output a control signal to sense a photo sensor located in a remaining one of the first area and the second area.

An embodiment of the present disclosure may provide a method of driving an electronic device including a processor and a display device configured to be controlled by the processor, the display device including a plurality of photo sensors and a readout circuit configured to sense signals from the plurality of photo sensors. The method may include: selecting from among a first mode and a second mode; and sensing, by the readout circuit, the signals from the plurality of photo sensors at a sensing resolution varying depending on a mode selected from among the first mode and the second mode.

The electronic device may further include a memory. The method may further include: executing first software stored in the memory according to the selected first mode; generating image data having a first sensing resolution according to the executed first software; and comparing the image data having the first sensing resolution with reference data pre-stored in the memory.

The electronic device may further include a memory. The method may further include: executing second software stored in the memory according to the selected second mode; generating a plurality of pieces of image data having a second sensing resolution according to the executed second software; and generating biometric signal data of a user of the electronic device, based on video data having the second sensing resolution and including the plurality of pieces of generated image data having the second sensing resolution.

A first photo sensor and a second photo sensor may be respectively disposed on different pixel rows in the display panel, and the readout circuit includes a capacitor element. The method may further include: storing a value acquired by sensing the first photo sensor in the selected first mode in the capacitor element; converting an analog voltage value including the value acquired by sensing the first photo sensor to a digital value, and outputting the digital value; storing a value acquired by sensing the signal from the second photo sensor in the selected first mode in the capacitor element; and converting an analog voltage value including the value acquired by sensing the signal from the second photo sensor to a digital value, and outputting the digital value.

A first photo sensor and a second photo sensor may be respectively disposed on different pixel rows in the display panel. The method may further include: storing a value acquired by sensing the signal from the first photo sensor in the selected second mode in a capacitor element; storing a value acquired by sensing the signal from the second photo sensor in the selected second mode in the capacitor element; and converting an analog voltage value including the value acquired by sensing the signal from the first photo sensor and the value acquired by sensing the signal from the second photo sensor to a digital value, and outputting the digital value.

The display panel may include a first area including any one of the plurality of photo sensors and at least one pixel. The method may further include: outputting, by the processor, image data to allow the least one pixel to emit light in the selected first mode; and outputting, by the processor, a control signal to sense a signal from any one photo sensor in the selected first mode.

The display panel may include a second area and a third area located around a peripheral area of the second area. Each of the second area and the third area may include any one of the plurality of photo sensors. Each of the second area and the third area may include at least one pixel. The method may further include: outputting, by the processor, image data to allow the pixel in any one of the second area and the third area to emit light in the selected second mode; and outputting, by the processor, a control signal to sense a signal of the photo sensor in a remaining one of the second area and the third area in the selected second mode.

BRIEF DESCRIPTION OF THE DRAWINGS

FIG. 2 is a diagram illustrating a display device and a processor in accordance with embodiments of the present disclosure.

FIG. 3 is a system diagram of a display device in accordance with embodiments of the present disclosure.

FIG. 7 is a diagram illustrating portions of the configuration of the pixel and the photo sensor in a sectional view of the display device in accordance with embodiments of the present disclosure.

DETAILED DESCRIPTION

Figure 1:
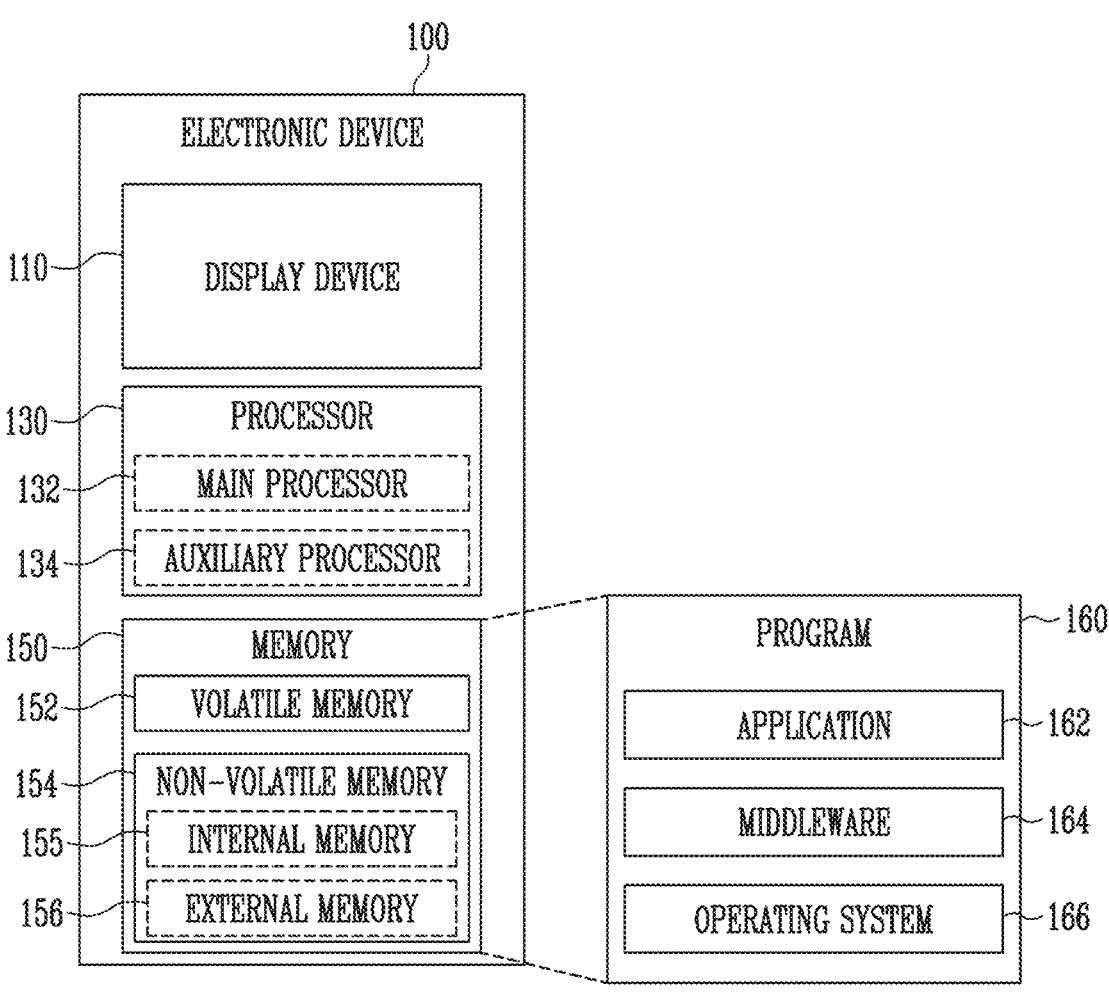
FIG. 1 is a schematic system diagram of an electronic device in accordance with embodiments of the present disclosure.

Hereinafter, embodiments of the present invention will be described in detail with reference to the attached drawings, such that those skilled in the art can easily implement the present invention. The present disclosure may be implemented in various forms, and is not limited to the embodiments to be described herein below.

In the drawings, portions which are not related to the present disclosure will be omitted in order to explain the present disclosure more clearly. Reference should be made to the drawings, in which similar reference numerals are used throughout the different drawings to designate similar components. Therefore, the aforementioned reference numerals may be used in other drawings.

For reference, the size of each component and the thicknesses of lines illustrating the component are arbitrarily represented for the sake of explanation, and the present disclosure is not limited to what is illustrated in the drawings. In the drawings, the thicknesses of the components may be exaggerated to clearly depict multiple layers and areas.

Furthermore, the expression "being the same" may mean "being substantially the same". In other words, the expression "being the same" may include a range that can be tolerated by those skilled in the art. The other expressions may also be expressions from which "substantially" has been omitted.

Hereinafter, embodiments of the present disclosure will be described in detail with reference to the attached drawings.

FIG. 1 is a schematic system diagram illustrating an electronic device 100 in accordance with embodiments of the present disclosure.

Referring to FIG. 1, the electronic device 100 in accordance with embodiments of the present disclosure may include a display device 110, a processor 130, and a memory 150.

The display device 110 may provide visual information to the outside (e.g., a user) of the electronic device 100. The display device 110 may include, for example, a display panel, a driving circuit, and the like. The display device 100 in accordance with embodiments of the present disclosure may include a touch sensor set to sense a touch, a pressure sensor set to measure the magnitude of force generated by the touch, and/or the like.

The processor 130 may execute, for example, software (e.g., a program 160) to control at least one other component (e.g., a hardware or software component) of the electronic device 100 connected to the processor 130, and may perform various data processing or computing operations. In accordance with embodiments of the present disclosure, as at least a portion of the data processing or computing operation, the processor 130 may store data received from other components (e.g., the display device 110) in a volatile memory 152, process a command or data stored in the volatile memory 152, and store result data in a non-volatile memory 154. In accordance with embodiments of the present disclosure, the processor 130 may include a main processor 132 (e.g., a central processing unit or an application processor) or an auxiliary processor 134 (e.g., a graphic processing unit (GPU), a neural processing unit (NPU), and an image signal processor, a sensor hub processor, a communication processor, or the like) capable of being operated independently or along with the main processor 132. For example, in the case where the electronic device 100 includes the main processor 132 and the auxiliary processor 134, auxiliary processor 134 may be operated with low power consumption compared to that of the main processor 132, or may be set to be specialized for a preset function. The auxiliary processor 134 may be implemented as a separate component from the main processor 132 or part of the main processor 132.

The auxiliary processor 134 may control a function or at least some states pertaining to at least one component (e.g., the display device 110) among components of the electronic device 100, for example, in lieu of the main processor 132 while the main processor 132 is in an inactive state (e.g., a sleeping state), or along with the main processor 132 while the main processor 132 is in an active state (e.g., an application executing state). In accordance with embodiments of the present disclosure, the auxiliary processor 134 (e.g., the image signal processor or the communication processor) may be implemented as a part of another component (e.g., a camera module (not illustrate), a communication module (not illustrated), or the like), which is functionally related thereto. In accordance with embodiments of the present disclosure, the auxiliary processor 134 (e.g., the neural processing unit) may include a hardware structure specialized for processing an artificial intelligence (AI) model. The AI model may be generated by machine learning.

The memory 150 may store various data to be used by at least one component (e.g., the processor 130) of the electronic device 100. The data may include, e.g., input data or output data for software (e.g., the program 160) and a command pertaining thereto. The memory 150 may include the volatile memory 152 or the non-volatile memory 154. The non-volatile memory 154 may include an internal memory 155. The non-volatile memory 154 may further include an external memory 156.

The program 160 may be stored as software in the memory 150, and may include, for example, an application 162, middleware 164, and an operating system 166.

The electronic device 100 in accordance with embodiments of the present disclosure may be referred to as a mobile station, mobile equipment (ME), user equipment (UE), a user terminal (UT), a subscriber station (SS), a wireless device, a handheld device, an access terminal (AT), or the like. The electronic device 100 in accordance with embodiments of the present disclosure may be a device such as a cellular phone, a personal digital assistant (PDA), a smart phone, a wireless modulator/demodulator (MODEM), or a notebook computer, having a communication function.

The electronic device 100 in accordance with embodiments of the present disclosure may include a power management module (not illustrated) configured to manage power to be supplied to the electronic device 100. The power management module may be implemented, for example, as at least a part of a power management integrated circuit (PMIC).

At least some of the components of the electronic device 100 in accordance with embodiments of the present disclosure may be connected to each other and exchange signals (e.g., a command or data) with each other through a communication scheme (e.g., a bus, general purpose input and output (GPIO), a mobile industry processor interface (MIPI), or the like) between peripheral devices.

Figure 2:
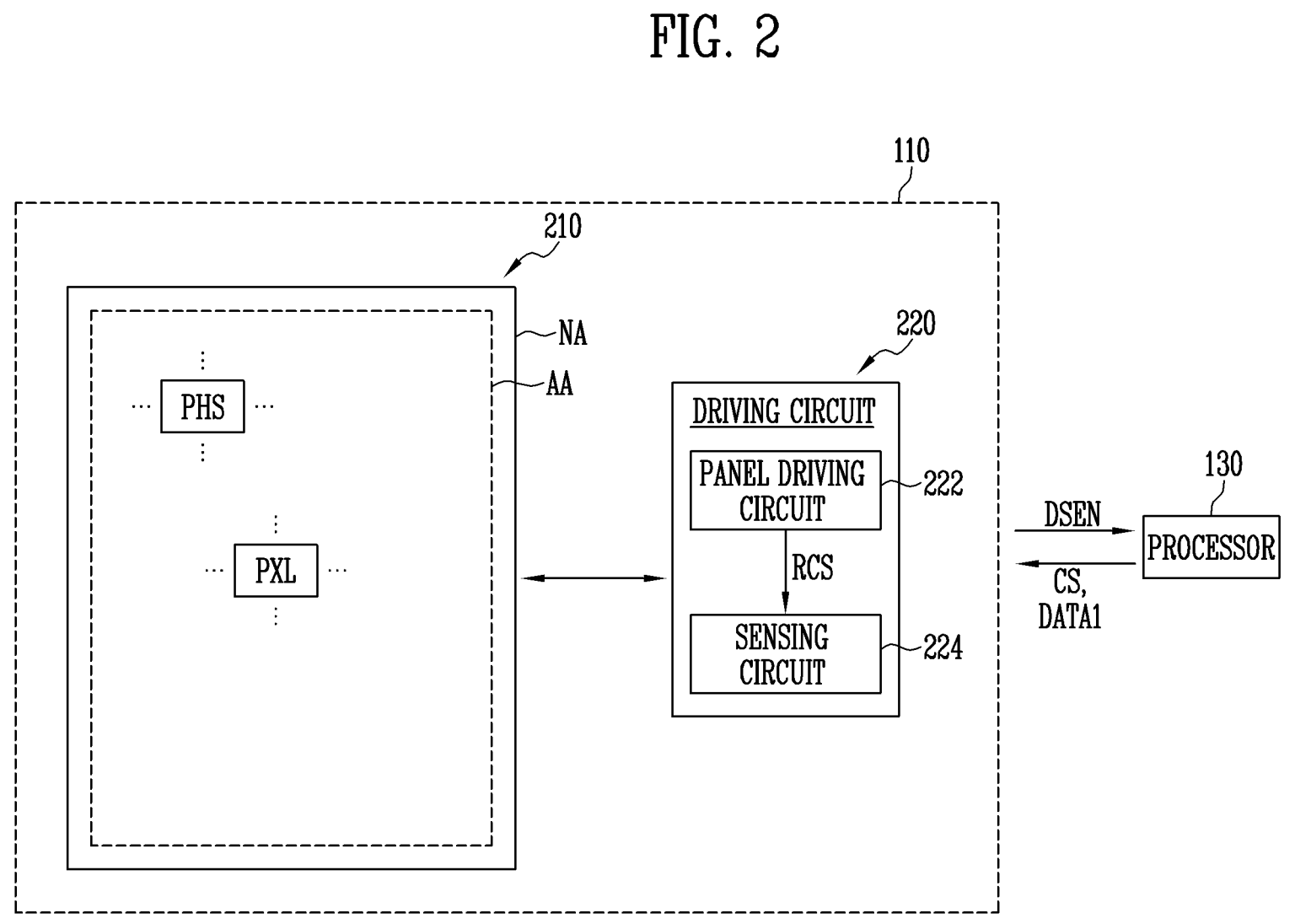

FIG. 2 is a diagram illustrating the display device 110 and the processor 130 in accordance with embodiments of the present disclosure.

Referring to FIG. 2, the display device 110 in accordance with embodiments of the present disclosure may include a display panel 210 and a driving circuit 220.

The display panel 210 may include a display area AA in which a pixel PXL is disposed, and a non-display area NA disposed in a peripheral area (e.g., an edge area) of the display area AA. One or more pixels PXL (e.g., a multiplicity of pixels PXL) may be disposed in the display area AA. One or more photo sensors PHS may be disposed in the display area AA.

The pixel PXL may be configured to display an image on the display device 110. To display information, the pixel PXL may emit light at luminance corresponding to a voltage inputted from the driving circuit 220. To display information, the voltage may be a data voltage. To output "transmitter light" to be directed towards a target object such as a finger's surface for a fingerprint measurement, or a capillary for a biometric parameter measurement, the voltage may be considered a control voltage.

The photo sensor PHS may be configured to detect a magnitude (intensity) of incident light, hereafter referred to as "a light receiving amount". The photo sensor PHS may include a light receiving element. The magnitude of current flowing through the photo sensor PHS (or flowing through the light receiving element) may depend on the intensity of light incident on the photo sensor PHS. Light incident on the photo sensor PHS may include reflective light. Here, the reflective light may be light emitted from pixels of the display device 110 and reflected by an external object (e.g., a human finger's surface, a human blood vessel wall, or a human's bone). The magnitude of current flowing through the photo sensor PHS may depend on the intensity of reflected light.

One or more pins (e.g., a pad) may be disposed in the non-display area NA. The display panel 210 and at least some components of the driving circuit 220 may be electrically connected to each other through the pins.

The driving circuit 220 may include a panel driving circuit 222 and a sensing circuit 224.

The panel driving circuit 222 may generate a signal for supplying a voltage to the display panel 210. For example, the driving circuit 220 may include a data driving circuit configured to output a data voltage, a scan driving circuit configured to supply a scan signal, an emission driving circuit configured to supply an emission signal, and the like. The driving circuit 220 may include, for example, a timing controller configured to control operation timings of the data driving circuit, the scan driving circuit, and the emission driving circuit.

The sensing circuit 224 may be configured to sense a signal from the photo sensor PHS disposed on the display panel 210.

The panel driving circuit 222 may output a readout circuit control signal RCS. The sensing circuit 224 may receive the readout circuit control signal RCS. A timing (or a length of a period) at which the sensing circuit 224 senses the photo sensor PHS may be controlled by the readout circuit control signal RCS.

The sensing circuit 224 may convert a value acquired by sensing the photo sensor PHS signal, to a corresponding digital value. As needed, the sensing circuit 224 may include an analog-to-digital converter (ADC) configured to convert an analog voltage value to a corresponding digital value DSEN. The sensing circuit 224 may output the converted digital value DSEN. The processor 130 may receive the digital value DSEN.

The processor 130 may output a control signal CS for controlling an operation timing of the driving circuit 220. The processor 130 may output first image data DATA1 to the driving circuit 220.

The driving circuit 220 may receive the control signal CS and the first image data DATA1 and display an image through the pixels PXL of the display panel 210, or may detect a light receiving amount through the photo sensor PHS of the display panel 210.

The processor 130 in accordance with embodiments of the present disclosure may generate an image or video based on the inputted digital value DSEN. For example, the processor 130 may generate an image having a first sensing resolution based on the inputted digital value DSEN. For example, the processor 130 may generate an image (or a video) having a second sensing resolution based on the inputted digital value DSEN. The video having the second sensing resolution may include two or more images of the second sensing resolution.

The first sensing resolution may be a relatively high resolution. The second sensing resolution may be a relatively low resolution.

In embodiments of the present disclosure, the processor 130 may output a control signal CS for generating an image having the first sensing resolution or output a control signal CS for generating an image having the second sensing resolution, depending on a selected mode (e.g., a mode selected by an input from the user of the electronic device).

Figure 3:
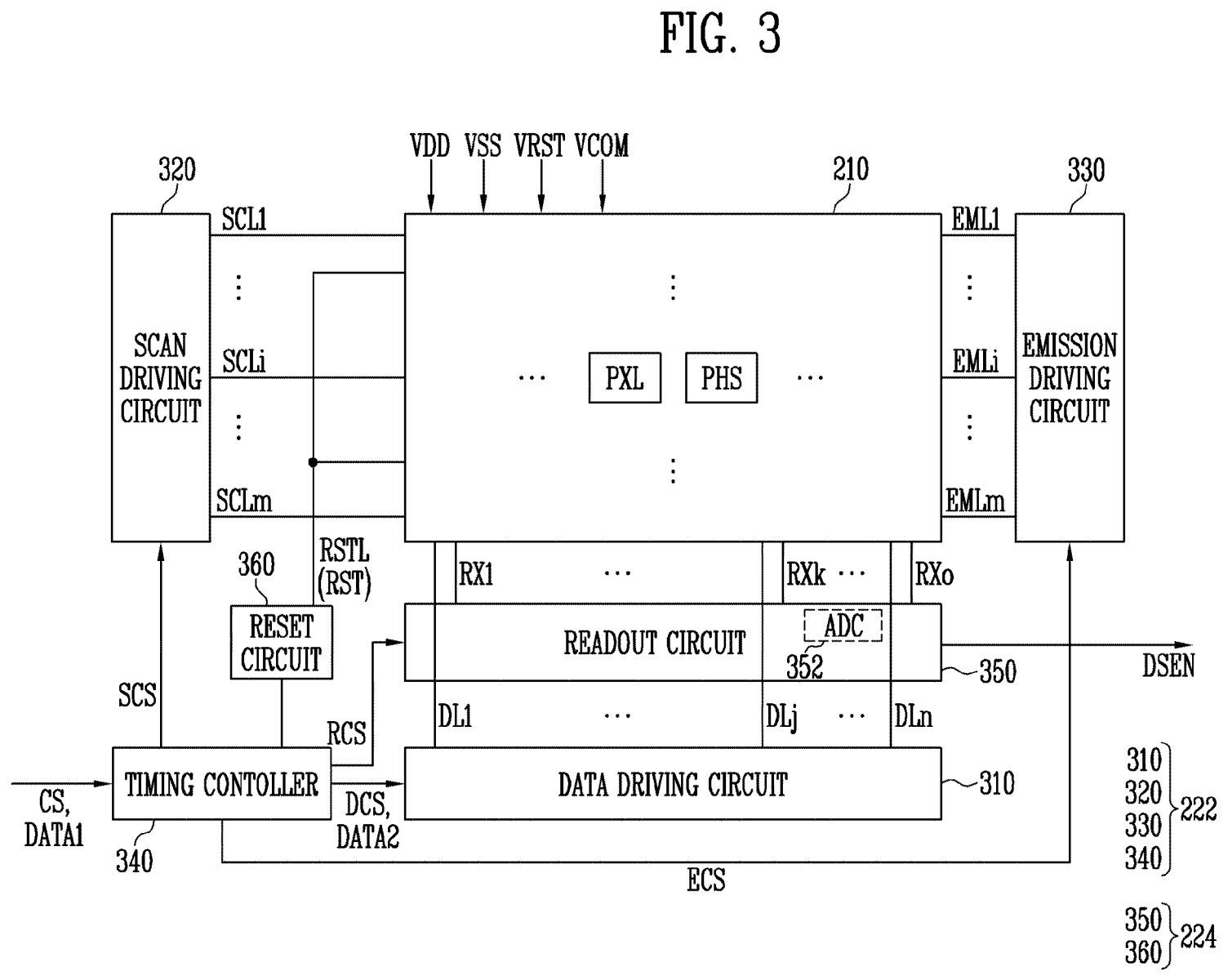

FIG. 3 is a system diagram of the display device 110 in accordance with embodiments of the present disclosure.

FIG. 3 is a system block diagram of the display device 110 described with reference to FIGS. 1 and 2.

Referring to FIG. 3, the display device in accordance with embodiments of the present disclosure may include a display panel 210, a data driving circuit 310, a scan driving circuit 320, an emission driving circuit 330, a timing controller 340, a readout circuit 350, a reset circuit 360, and the like.

The panel driving circuit 222 described above may include a data driving circuit 310, a scan driving circuit 320, an emission driving circuit 330, a timing controller 340, and the like. The sensing circuit 224 described above may include a readout circuit 350, a reset circuit 360, and the like.

One or more pixels PXL may be disposed in the display panel 210. One or more photo sensors PHS may be disposed in the display panel 210. One or more "power voltages" may be supplied to the display panel 210, where a "power voltage" herein may refer to a voltage applied to the pixel PXL and/or the photo sensor PHS.

The power voltages may include a first power voltage VDD, a second power voltage VSS, a third power voltage VRST, a fourth power voltage VCOM, and the like. Each of the power voltages may be commonly applied to a plurality of pixels PXL and/or a plurality of photo sensors PHS, and may be referred to as a common voltage. For example, the power voltages may be generated from a power managing module.

A plurality of data lines DL1 to DLn (here, n is an integer of 2 or more) may be disposed in the display panel 210. The plurality of data lines DL1 to DLn may be disposed in the display panel 210 and extend in a first direction. The first direction may be, for example, a direction (e.g., a column direction) perpendicular to each of an upper side and a lower side of the display panel 210, or may be a direction (e.g., a row direction) perpendicular to each of a left side and a right side of the display panel 210. In the following description, for simplicity of explanation, the first direction is described as the direction perpendicular to the upper and lower sides, but the first direction may differ in other embodiments.

A plurality of scan lines SCL1 to SCLm (here, m is an integer of 2 or more) may be disposed in the display panel 210. The plurality of scan lines SCL1 to SCLm may be disposed in the display panel 210 and extend in a second direction. The second direction may be, for example, a direction perpendicular to each of the left and right sides of the display panel 210 are connected to each other, and a direction in which the upper side and the lower side of the display panel 210 are connected to each other. For instance, the second direction may be perpendicular to the first direction. In the following description, for simplicity of explanation, the second direction is described as the direction perpendicular to each of the left and right sides of the display panel 210, but the second direction may differ in other embodiments.

The phrase "disposed to extend in the first direction" may mean that lines are disposed to generally extend in a direction in which the upper side and the lower side are connected to each other, and may not exclude that the lines partially extend in other directions different from the first direction. For example, in embodiments of the present disclosure, at least one data line of the plurality of data lines DL1 to DLn may be designed to partially detour and extend in a direction different from the first direction and thus avoid a specific area (e.g., a high transmittance area). The phrase "disposed to extend in the second direction" may also be used in the same sense as the phrase "disposed to extend in the first direction".

A plurality of emission lines EML1 to EMLm may be disposed in the display panel 210. The plurality of emission lines EML1 to EMLm may be disposed in the display panel 210 and extend in the second direction.

A plurality of sensing lines RX1 to RXo (here, o is an integer of 2 or more) may be disposed in the display panel 210. The plurality of sensing lines RX1 to RXo may be disposed in the display panel 210 and extend in the first direction DR1.

At least one reset control line RSTL may be disposed in the display panel 210.

Each pixel PXL may be electrically connected to a data line among the data lines DL1 to DLn. The pixel PXL may be electrically connected to at least one scan line of the plurality of scan lines SCL1 to SCLm. The pixel PXL may be electrically connected to at least one emission line of the plurality of emission lines EML1 to EMLm.

Each photo sensor PHS may be electrically connected to a sensing line among the sensing lines RX1 to RXo. The photo sensor PHS may be electrically connected to the reset control line RSTL. The photo sensor PHS may be electrically connected to at least one scan line of the scan lines SCL1 to SCLm.

The pixel PXL and the photo sensor PHS may be electrically connected to any one scan line of the plurality of scan lines SCL1 to SCLm. The pixel PXL may be electrically connected to any one emission line of the plurality of emission lines EML1 to EMLm.

In an embodiment, the plurality of pixels PXL may be disposed in the form of a matrix in the display panel 210. In the form of a matrix, the plurality of pixels PXL may be disposed in an RGBG-type array, or may be disposed to have a PENTILE™ structure having a rhombus shape.

The data driving circuit 310 may be configured to supply data voltages to the plurality of data lines DL1 to DLn. The data driving circuit 310 may receive a data driving circuit control signal DCS and second image data DATA2, and supply data voltages corresponding to the image data to the plurality of data lines DL1 to DLn at correct timings.

The scan driving circuit 320 may be configured to supply scan signals to the plurality of scan lines SCL1 to SCLm. In an embodiment, the scan driving circuit 320 may be configured to sequentially supply scan signals to the plurality of scan lines SCL1 to SCLm, but is not limited thereto. The scan driving circuit 320 may receive a scan driving circuit control signal SCS, and supply scan signals to the plurality of scan lines SCL1 to SCLm at correct timings.

The emission driving circuit 330 may be configured to supply emission signals to the plurality of emission lines EML1 to EMLm. The emission driving circuit 330 may be configured to sequentially supply emission signals to the plurality of emission lines EML1 to EMLm, but is not limited thereto. The emission driving circuit 330 may receive an emission driving circuit control signal ECS, and supply emission signals to the plurality of emission lines EML1 to EMLm at correct timings.

The timing controller 340 may receive a control signal CS and first image data DATA1, and may generate and output a data driving circuit control signal DCS, a scan driving circuit control signal SCS, an emission driving circuit control signal ECS, second image data DATA2, a readout circuit control signal RCS, and the like, based on the inputted control signal CS and the first image data DATA1.

The readout circuit 350 may be electrically connected to a plurality of sensing lines RX1 to RXo. The readout circuit 350 may be configured to sense a plurality of photo sensors PHS through the plurality of sensing lines RX1 to RXo. For example, depending on the design of the readout circuit 350, the readout circuit 350 may integrate current flowing through at least one of the plurality of sensing lines RX1 to RXo (i.e., through a current sensing scheme), or may sense a voltage of at least one of the plurality of sensing lines RX1 to RXo (i.e., through a voltage sensing scheme). The readout circuit 350 may include a multiplexer (not illustrated) configured to integrate the current (or sense the voltage) of at least one of the plurality of sensing lines RX1 to RXo. Although hereinafter for convenience of explanation the case where the readout circuit 350 employs the current sensing scheme will be described by way of example, embodiments of the present disclosure is not limited thereto.

The readout circuit 350 may include an analog-to-digital converter (ADC) 352 configured to convert a sensed analog voltage to a digital value DSEN.

The reset circuit 360 may be configured to supply a reset signal RST to the plurality of photo sensor PHS. If the reset signal RST is supplied to the photo sensor PHS, electrical connection between the photo sensor PHS and the sensing line (e.g., a k-th sensing line RXk) may be disconnected. A timing at which the reset circuit 360 outputs the reset signal RST may be controlled by the timing controller 340.

One or more circuits that constitute the panel driving circuit 222 may be disposed in the display device in the form of an integrated circuit (IC). For example, the data driving circuit 310 may include a source driver integrated circuit (SDIC).

The one or more circuits that constitute the panel driving circuit 222 may be formed together during a process of forming the display panel 210. For example, the scan driving circuit 320 may be formed together during a process of forming one or more circuit elements (e.g., a transistor, and the like) included in the pixel PXL and/or the photo sensor PHS.

The data driving circuit 310, the scan driving circuit 320, and the emission driving circuit 330, and the timing controller 340 are classified only according to the function in the panel driving circuit 222, and two or more components may be components which are functionally distinguished from each other in a single integrated circuit. For example, the data driving circuit 310 and the timing controller 340 may be implemented as a single integrated circuit, and may be functionally distinguished from each other in the integrated circuit. For instance, the scan driving circuit 320 and the emission driving circuit 330 may be implemented as a single integrated circuit, and may be functionally distinguished from each other in the integrated circuit.

The panel driving circuit 222 and the sensing circuit 224 are classified only according to the function in the display device, and the panel driving circuit 222 and the sensing circuit 224 may be functionally distinguished from each other in a single integrated circuit. For example, the panel driving circuit 222 and the sensing circuit 224 may be respectively implemented in different integrated circuits, but in some cases, the panel driving circuit 222 and the sensing circuit 224 may be functionally distinguished from each other in a single integrated circuit.

Figure 4:
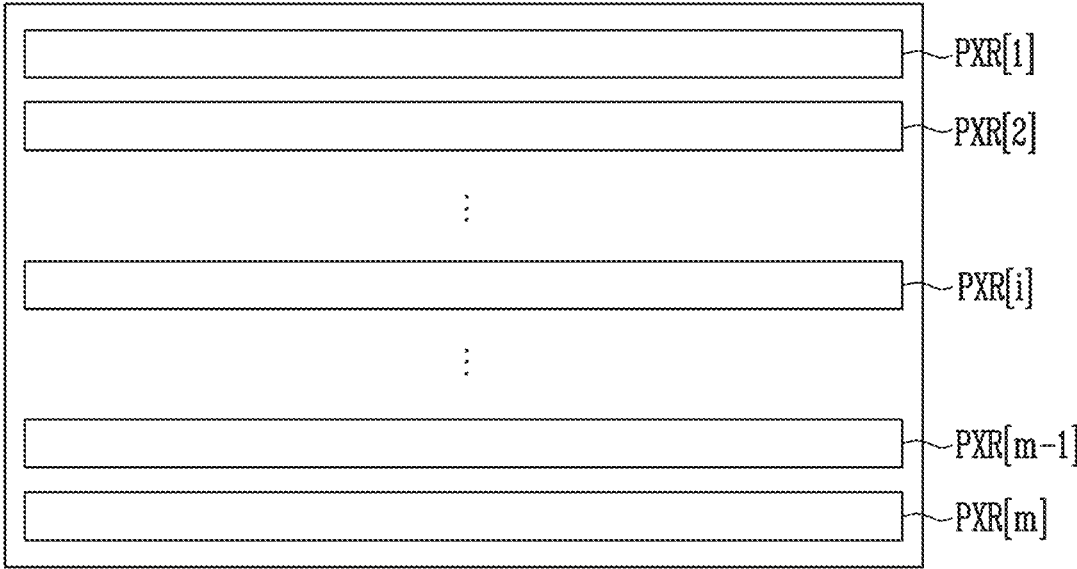
FIG. 4 is a diagram illustrating a pixel row in accordance with embodiments of the present disclosure.

FIG. 4 is a diagram illustrating example pixel rows in accordance with embodiments of the present disclosure. Each of a plurality of pixel rows PXR[1] to PXR[m] may include two or more pixels.

At least one of the pixel rows PXR[1] to PXR[m] may include a photo sensor PHS (shown in FIG. 2). In an embodiment, each of pixel rows PXR[1] to PXR[m] includes a photo sensor PHS. In another embodiment, some of the pixel rows PXR[1] to PXR[m] include a photo sensor, and remaining pixel rows do not include a photo sensor.

Two or more pixels included in each pixel row (e.g., an i-th pixel row PXR[i] (i is an integer of $1 \leq i \leq m$)) may be electrically connected to one scan line.

In a pixel row (e.g., an i-th pixel row PXR[i]) including a photo sensor, two or more pixels and the photo sensor may be electrically connected to one scan line.

Figure 5:
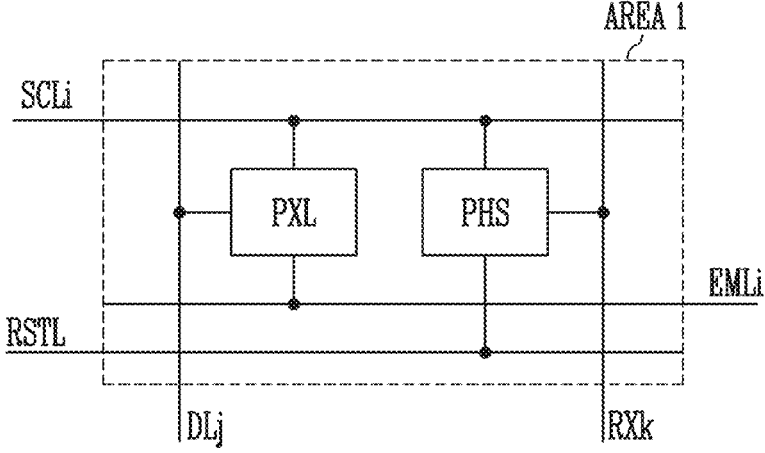
FIG. 5 is a diagram illustrating a pixel and a photo sensor which are located in a first area in accordance with embodiments of the present disclosure.

FIG. 5 is a diagram illustrating a pixel PXL and a photo sensor PHS which are located in a first area AREA 1 in accordance with embodiments of the present disclosure. The first area AREA 1 may be a sub-area of the display area AA, and may be an area large enough for a user to place his/her finger thereon for at least a fingerprint authentication measurement and, in some embodiments, a biometric parameter measurement.

The first area AREA 1 may include an area in which an i-th scan line SCLi is disposed, an i-th emission line EMLi is disposed, a j-th data line DLj (j is an integer of $1 \leq j \leq n$) is disposed, and a k-th sensing line RXk is disposed. The first area AREA 1 may include an area in which a reset control line RSTL is disposed.

Figure 19:
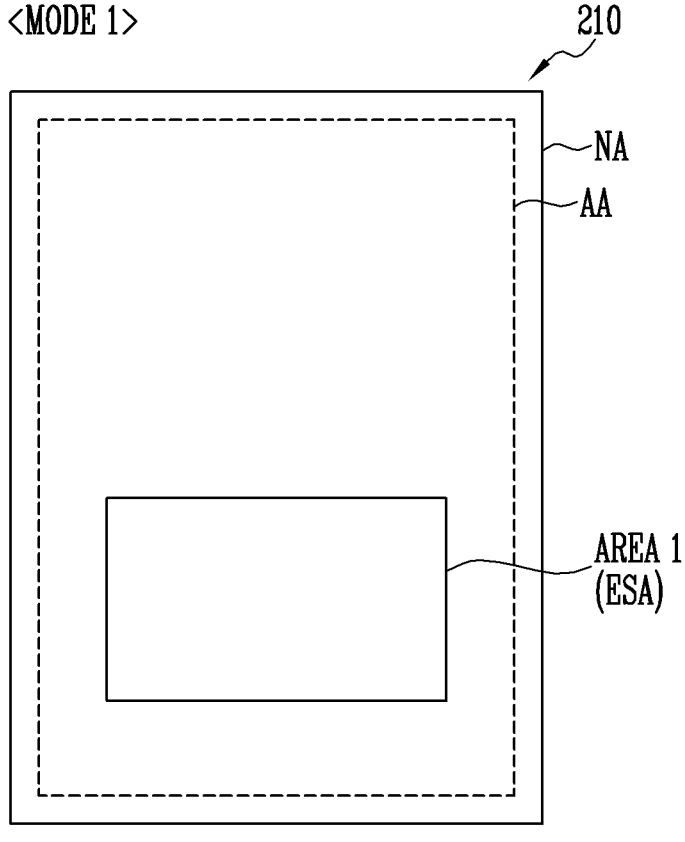
FIG. 19 is a diagram illustrating that the first area includes an emitting-sensing area in the case where the first mode is selected, in accordance with embodiments of the present disclosure.

The pixel PXL located in the first area AREA 1 may be electrically connected to the i-th scan line SCLi, the i-th emission line EMLi, and the j-th data line DLj. The photo sensor PHS located in the first area AREA 1 may be electrically connected to the i-th scan line SCLi, the k-th sensing line RXk, and the reset control line RSTL. Although only one pixel PXL and one photo sensor PHS are illustrated in the first area AREA 1 in FIG. 5, the first area AREA 1 may include multiple pixels PXL in each of a plurality of adjacent rows, and multiple photo sensors PHY in each of a plurality of adjacent rows. An example of the first area AREA 1 relative to the display area AA is illustrated in FIG. 19 discussed later.

Figure 6:
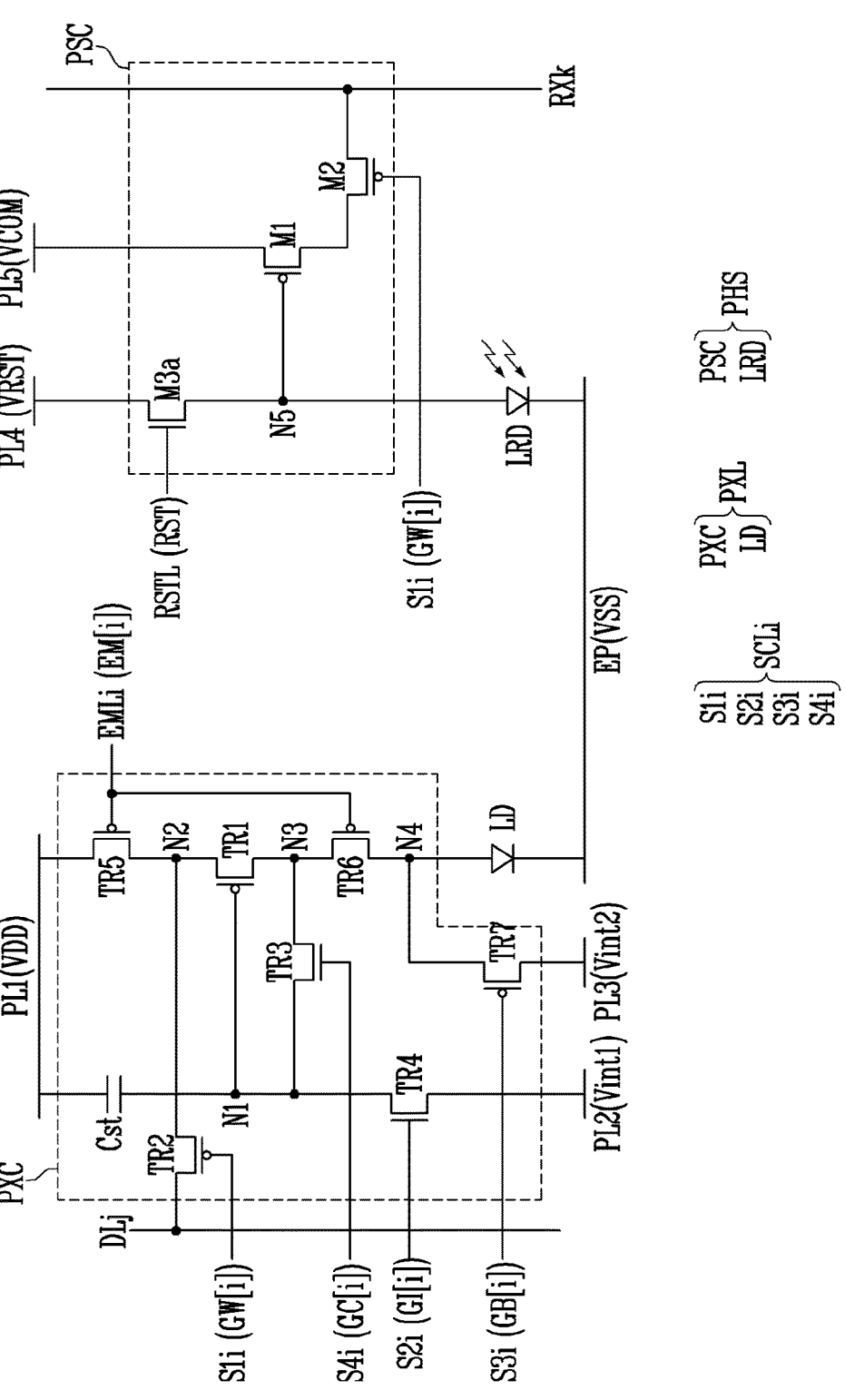
FIG. 6 is a diagram illustrating an equivalent circuit of the pixel and an equivalent circuit of the photo sensor in accordance with embodiments of the present disclosure.

FIG. 6 is a diagram illustrating an equivalent circuit of the pixel PXL and an equivalent circuit of the photo sensor PHS in accordance with embodiments of the present disclosure.

Referring to FIG. 6, the pixel PXL may include a pixel driving circuit PXC and a light emitting element LD. The photo sensor PHS may include a photo sensor driving circuit PSC and a light receiving element LRD.

The pixel driving circuit PXC may be configured to adjust the magnitude of current flowing through the light emitting element LD. The pixel driving circuit PXC may include two or more transistors and one or more capacitors. Although the pixel driving circuit PXC may be implemented in various ways according to the design of those skilled in this art, a structure (referred also to as a 7T1C structure) in which the pixel driving circuit PXC includes seven transistors and one capacitor will be described by way of example with reference to the equivalent circuit illustrated in FIG. 6. This type of structure, through use of an emission line EML voltage, may compensate for a threshold voltage (Vth) shift of a thin film transistor (TFT) for driving an organic LED, improving uniformity of luminance.

The pixel driving circuit PXC may include first to seventh transistors TR1 to TR7 and one capacitor Cst. The first pixel transistor TR1 may be configured to switch electrical connection between a second node N2 and a third node N3 in response to a voltage of a first node N1. The first node N1 may be electrically connected to a gate electrode of the first pixel transistor TR1. The second node N2 may be electrically connected to a source or drain electrode of the first pixel transistor TR1. The third node N3 may be electrically connected to the other of the source or drain electrode of the first pixel transistor TR1. Depending on the magnitude of a voltage to be applied to the first node N1, the magnitude of current flowing through the first pixel transistor TR1 (and the magnitude of current flowing through the light emitting element LD) may be controlled. The first driving transistor TR1 may also be referred to as a driving transistor.

The second pixel transistor TR2 may be configured to switch electrical connection between the second node N2 and a data line DLj. The second pixel transistor TR2 may be configured to transmit a voltage (e.g., a data voltage) to be applied to the data line DLj, to the second node N2 in response to a first scan signal GW[i] of a turn-on level. The first scan signal GW[i] may be applied to a first scan line S1*i*.

The third pixel transistor TR3 may be configured to switch electrical connection between the first node N1 and the third node N3. The third pixel transistor TR3 may switch the electrical connection between the first node N1 and the third node N3 in response to a fourth scan signal GC[i]. The fourth scan signal GC[i] may be applied to a fourth scan line S4*i*. If the third pixel transistor TR3 is turned on, the first pixel transistor TR1 may be operated in the same manner as that of a diode.

The fourth pixel transistor TR4 may be configured to switch electrical connection between the first node N1 and a second power line PL2. The fourth pixel transistor TR4 may switch the electrical connection between the first node N1 and the second power line PL2 in response to a second scan signal GI[i]. The second scan signal GI[i] may be applied to the second scan line S2*i*. A first initialization voltage Vint1 may be applied to the second power supply line PL2. If the fourth pixel transistor TR4 is turned on, the voltage of the first node N1 may be initialized to a first initialization voltage Vint1.

The fifth pixel transistor TR5 may be configured to switch electrical connection between the second node N2 and a first power line PL1. The fifth pixel transistor TR5 may switch electrical connection between the second node N2 and the first power line PL1 in response to an emission signal EM[i]. If the fifth pixel transistor TR5 is turned on, a first power voltage VDD may be applied to the second node N2.

The sixth pixel transistor TR6 may be configured to switch electrical connection between the third node N3 and a fourth node N4. The sixth pixel transistor TR6 may switch electrical connection between the third node N3 and the fourth node N4 in response to an emission signal EM[i]. Referring to FIG. 6, the sixth pixel transistor TR6 and the fifth pixel transistor TR5 may be electrically connected to the same emission line EMLi.

The seventh pixel transistor TR7 may be configured to switch electrical connection between the fourth node N4 and a third power line PL3. The seventh pixel transistor TR7 may switch the electrical connection between the fourth node N4 and the third power line PL3 in response to a third scan signal GB[i]. If the seventh pixel transistor TR7 is turned on, the voltage of the fourth node N4 may be initialized to a second initialization voltage Vint2.

The capacitor Cst may be configured to supply a voltage to the first node N1 during one frame period. The capacitor Cst may include a first side electrode electrically connected to the first node N1, and a second side electrode electrically connected to a power line (e.g., the first power line PL1). A data voltage (or a voltage derived from the data voltage) may be applied to the first side electrode of the capacitor Cst. The capacitor Cst may supply a voltage to the first node N1 during one frame period. The capacitor Cst may also be referred to as a storage capacitor.

Each of the first to seventh pixel transistors TR1 to TR7 may be an n-type transistor or a p-type transistor.

In the n-type transistor, a turn-on level voltage may be a high logic level voltage, and a turn-off level voltage may be a low logic level voltage. In the p-type transistor, a turn-on level voltage may be a low logic level voltage, and a turn-off level voltage may be a high logic level voltage.

In the example of FIG. 6, the third pixel transistor TR3 and the fourth pixel transistor TR4 among the first to seventh pixel transistor TR1 to TR7 are n-type transistors, and the other pixel transistors are p-type transistors. In other embodiments, different selections among n-type and p-type transistors may be made.

One or more transistors of the first to seventh pixel transistors TR1 to TR7 may include an oxide semiconductor (or an oxide semiconductor layer). One or more transistors of the first to seventh pixel transistors TR1 to TR7 may include a silicon semiconductor (e.g., an amorphous silicon (a-Si) semiconductor or a low temperature polycrystalline silicon (LTPS) semiconductor). For example, although each of the third pixel transistor TR3 and the fourth pixel transistor TR4 includes an oxide semiconductor, embodiments of the present disclosure are not limited thereto.

The light emitting element LD may be connected between the fourth node N4 and a sixth power line EP. The fourth node N4 may be electrically connected to an anode electrode of the light emitting element LD. The sixth power line EP may be electrically connected to a cathode electrode of the light emitting element LD.

The light emitting element LD may include a light emitting layer. Depending on the kind of the light emitting layer, the light emitting element LD may be implemented as an organic light emitting element including an organic light emitting layer, an inorganic light emitting element including an inorganic light emitting layer, a quantum dot light emitting element including a quantum dot (e.g., a nanorod), or the like.

The single pixel driving circuit PXC may be connected to two or more light emitting elements LD. The two or more light emitting elements LD may be connected in series and/or parallel to each other.

The photo sensor driving circuit PSC may include first to third sensor transistors M1, M2, and M3*a*.

The first sensor transistor M1 may be configured to switch electrical connection between a fifth power line PL5 and the second sensor transistor M2. The first sensor transistor M1 may be configured to switch electrical connection between the fifth power line PL5 and the second sensor transistor M2 depending on the voltage level of a fifth node N5. The fourth power voltage VCOM may be applied to the fifth power supply line PL5.

The second sensor transistor M2 may be configured to switch electrical connection between the first sensor transistor M1 and the sensing line RXk. The second sensor transistor M2 may electrically connect the first sensor transistor M1 and the sensing line RXk to each other in response to a scan signal (e.g., a first scan signal GW[i]).

The third sensor transistor M3a may be configured to switch electrical connection between the fourth power line PL4 and the fifth node N5. The third sensor transistor M3a may be configured to switch electrical connection between the fourth power line PL4 and the fifth node N5 in response to a reset signal RST. If the third sensor transistor M3a is turned on, the voltage of the fifth node N5 may be initialized to the third power voltage VRST. The third power voltage VRST may be a turn-on level voltage (e.g., a low logic level voltage) of the first sensor transistor M1.

Each of the first to third sensor transistors M1, M2, and M3a may be implemented as a p-type transistor or an n-type transistor. Each of the first to third sensor transistors M1, M2, and M3a may include any one of an amorphous silicon semiconductor, a low temperature poly silicon semiconductor, and an oxide semiconductor.

Although referring to FIG. 6 there is illustrated the case where the third sensor transistor M3a is implemented as an n-type transistor and the first second transistor M1 and the second sensor transistor M2 are implemented as p-type transistors, embodiments of the present disclosure are not limited thereto.

The light receiving element LRD may electrically connect the fifth node N5 and the sixth power line EP to each other in response to light. For example, the light receiving element LRD may be implemented as a photo diode.

A simple description of a process in which current flows through the sensing line RXk in accordance with embodiments of the present disclosure is as follows.

In embodiments of the present disclosure, if light is applied to the light receiving element LRD, current may flow through the light receiving element LRD. If current flows through the light receiving element LRD, the voltage of the fifth node N5 may be gradually reduced. If the voltage of the fifth node N5 is gradually reduced and is thus less than a value less than a threshold voltage of the first sensor transistor M1, the first sensor transistor M1 may be turned on. If a first scan signal GW[i] of a turn-on level is applied to the second sensor transistor M2, the second sensor transistor M2 may be turned on. Thereby, if the first sensor transistor M1 and the second sensor transistor M2 are turned on, a current path extending from the fifth power line PL5 to the sensing line RXk may be formed. The quantity of light that is incident on the light receiving element LRD may be calculated by integrating current flowing through the sensing line RXk (or by sensing a voltage applied thereto).

In embodiments of the present disclosure, the intensity of reflective light reflected by an object adjacent to the photo sensor PHS may be measured by using the photo sensor PHS.

In the electronic device in accordance with embodiments of the present disclosure, a pattern of an object (e.g., a pattern of a fingerprint) adjacent to the photo sensor PHS may be acquired (or generated) by sensing a signal from the photo sensor PHS. Hence, the electronic device in accordance with embodiments of the present disclosure may provide a biometric authentication function (e.g., a fingerprint authentication function).

In an optical detection method for measuring a biometric parameter (interchangeably, "biometric signal"), an optical signal such as a red color signal or infrared signal may be output towards a target object such as a user's capillary, and a reflection from the object may be sensed to capture a video representing movement of the target object, to measure the biometric parameter. For instance, a video representing expansion and contraction of a capillary may be analyzed to measure heart rate, where the expansion and contraction may correspond to changes in optical intensity received at a photo sensor. In the electronic device in accordance with embodiments of the present disclosure, through use of the optical detection method, a trending change in the magnitude of light reflected by the target object adjacent to the photo sensor PHS (e.g., correlated with a trending change in distance from the photo sensor to a wall of a capillary vessel of the user) may be calculated by sensing signals from the photo sensor PHS. Hence, the electronic device in accordance with embodiments of the present disclosure may provide a function of measuring a biometric signal (e.g., a heart rate, blood pressure, oxygen saturation, or the like).

Figure 7:
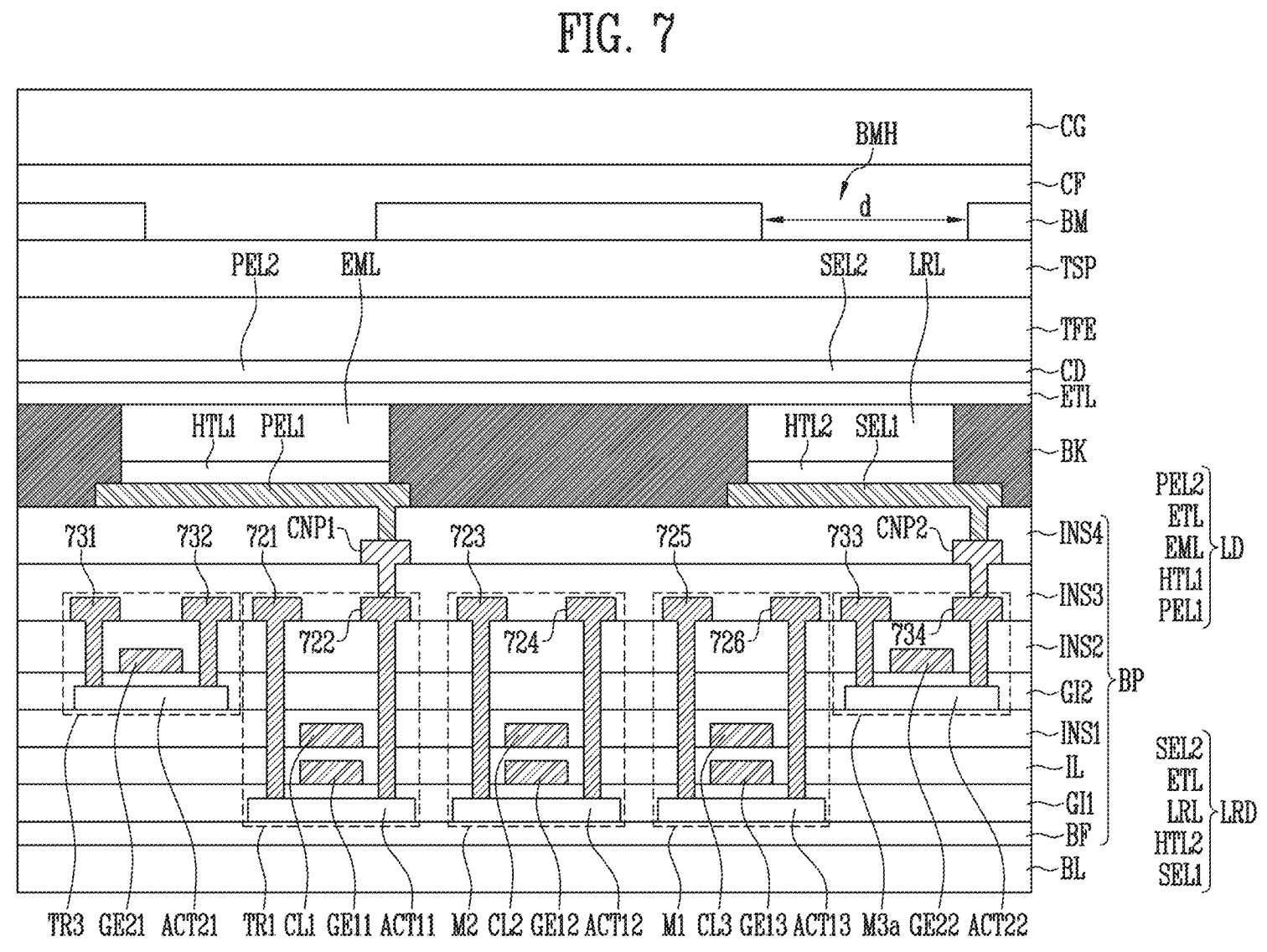

FIG. 7 is a diagram illustrating portions of the configuration of the pixel and the photo sensor in a sectional view of the display device in accordance with embodiments of the present disclosure.

Referring to FIGS. 1 to 7, the pixel transistors TR1 to TR7 and the sensor transistors M1, M2, and M3a may be included in a backplane structure BP (or a circuit layer) of the display panel 210.

FIG. 7 illustrates the first pixel transistor TR1, the third pixel transistor TR3, the first sensor transistor M1, the second sensor transistor M2, and the third sensor transistor M3.

The base layer BL may be made of insulating material such as glass or resin. Furthermore, the base layer BL may be made of material having flexibility so as to be bendable or foldable, and have a single layer or multilayer structure.

The backplane structure BP including a pixel driving circuit and a sensor driving circuit may be provided on the base layer BL. The backplane structure BP may include a semiconductor layer, a plurality of conductive layers, and a plurality of insulating layers which will be described below. For example, the base layer BL may include a first base layer, a second base layer, a second barrier layer, and the like, which are successively stacked. The first base layer and the second base layer each may include polyimide (PI), polyethersulfone (PES), polyarylate, polyetherimide (PEI), polyethylene naphthalate (PEN), polyethyleneterephthalate (PET), polyphenylene sulfide (PPS), polycarbonate (PC), cellulose triacetate (CTA), and/or cellulose acetate propionate (CAP), and the like. The first barrier layer and the second barrier layer may include inorganic insulating material such as silicon oxide, silicon oxynitride, and/or silicon nitride. The base layer BL may be flexible.

A buffer layer BF may be formed on the base layer BL. The buffer layer BF may prevent impurities from diffusing into the pixel transistors (e.g., the first to seventh pixel transistors TR1 to TR7) and the sensor transistors (e.g., the first to third sensor transistors M1, M2, and M3a). The buffer layer BF may be omitted depending on the material of the base layer BL or processing conditions. The buffer layer BF may include inorganic insulating material such as silicon oxide, silicon oxynitride, or silicon nitride. The buffer layer BF may have a single-layer structure or multilayer structure including the foregoing material. The buffer layer BF may be omitted depending on the material of the base layer BL or processing conditions.

First to third active patterns ACT11, ACT12, and ACT13 may be provided on the buffer layer BF. In an embodiment, the first to third active patterns ACT11, ACT12, and ACT13 each may be formed of a poly-silicon semiconductor. For example, the first to third active patterns ACT11, ACT12, and ACT13 may be formed, for example, through a low-temperature polycrystalline silicon (LTPS) process.

A first gate insulating layer GI1 may be provided on the first to third active patterns ACT11, ACT12, and ACT13. The first gate insulating layer GI1 may be formed of an inorganic insulating layer including inorganic material. The first gate insulating layer GI1 may include inorganic insulating material such as silicon oxide ($SiO_2$), silicon nitride ($SiN_x$) (x is a positive number), silicon oxynitride (SiON), aluminum oxide ($Al_2O_3$), titanium oxide ($TiO_2$), tantalum oxide ($Ta_2O_5$), hafnium oxide ($HfO_2$), and/or zinc oxide ($ZnO_2$).

The first to third gate electrodes GE11, GE12, and GE13 may be provided on the first gate insulating layer GI1. The first gate electrode GE11 may overlap the channel area of the first active pattern ACT11. The second gate electrode GE12 may overlap the channel area of the second active pattern ACT12. The third gate electrode GE13 may overlap the channel area of the third active pattern ACT13.

The first to third gate electrodes GE11, GE12, and GE13 each may be formed of metal. For example, the first to third gate electrodes GE11, GE12, and GE13 each may be made of at least one of metals such as gold (Au), silver (Ag), aluminum (Al), molybdenum (Mo), chrome (Cr), titanium (Ti), nickel (Ni), neodymium (Nd), copper (Cu), and an alloy of the metals. Furthermore, the first to third gate electrodes GE11, GE12, and GE13 each may have a single-layer structure, or may have a multilayer structure formed by stacking layers made of two or more materials of metals and alloys.

An interlayer insulating layer IL may be provided on the first to third gate electrodes GE11, GE12, and GE13. The interlayer insulating layer IL may be formed of an inorganic insulating layer including inorganic material. Polysiloxane, silicon nitride, silicon oxide, silicon oxynitride, or the like may be used as the inorganic material.

Conductive patterns CL1, CL2, and CL3 may be provided on the interlayer insulating layer IL. Referring also to FIG. 6, the conductive patterns CL1, CL2, and CL3 each may form at least one among one electrode of the capacitor Cst, the scan lines (e.g., the first to fourth scan lines S1$i$ to S4$i$), the reset control line RSTL, the data line DLj, the sensing line RXk, and the power lines (e.g., PL1 to PL5).

The conductive patterns CL1, CL2, and CL3 may be made of at least one of metals such as gold (Au), silver (Ag), aluminum (Al), molybdenum (Mo), chrome (Cr), titanium (Ti), nickel (Ni), neodymium (Nd), copper (Cu), or an alloy of the metals. The conductive patterns CL1, CL2, and CL3 each may have a single-layer structure, or may have a multilayer structure formed by stacking two or more materials of metals and alloys.

The first insulating layer INS1 may be provided on the conductive patterns CL1, CL2, and CL3. The first insulating layer INS1 may be formed of an inorganic insulating layer including inorganic material. Polysiloxane, silicon nitride, silicon oxide, silicon oxynitride, or the like may be used as the inorganic material.

A fourth active pattern ACT21 and a fifth active pattern ACT22 may be provided on the first insulating layer INS1. In an embodiment, the fourth and fifth active patterns ACT21 and ACT22 each may be formed of an oxide semiconductor. For example, the fourth and fifth active patterns ACT21 and ACT22 each may be formed through a metal oxide semiconductor forming process.

A second gate insulating layer GI2 may be provided on the fourth active pattern ACT21 and the fifth active pattern ACT22. The second gate insulating layer GI2 may be formed of an inorganic insulating layer including inorganic material. For example, one or more of polysiloxane, silicon nitride, silicon oxide, and silicon oxynitride may be used as the inorganic material.

The fourth and fifth gate electrodes GE21 and GE22 may be provided on the second gate insulating layer GI2. The fourth gate electrode GE21 may overlap the channel area of the fourth active pattern ACT21. The fifth gate electrode GE22 may overlap the channel area of the fifth active pattern ACT22. The fourth and fifth gate electrodes GE21 and GE22 each may be formed of metal. For example, the fourth and fifth gate electrodes GE21 and GE22 each may be made of at least one of metals such as gold (Au), silver (Ag), aluminum (Al), molybdenum (Mo), chrome (Cr), titanium (Ti), nickel (Ni), neodymium (Nd), copper (Cu), and an alloy of the metals. Furthermore, the fourth and fifth gate electrodes GE21 and GE22 each may have a single-layer structure, or may have a multilayer structure formed by stacking layers made of two or more materials of metals and alloys.

The second insulating layer INS2 may be provided on the fourth and fifth gate electrodes GE21 and GE22. For example, the second insulating layer INS2 may be formed of an inorganic insulating layer including inorganic material. For example, one or more of polysiloxane, silicon nitride, silicon oxide, and silicon oxynitride may be used as the inorganic material.

First source/drain electrodes 721 and 722 (e.g., a first source electrode 721 and a first drain electrode 722), second source/drain electrodes 723 and 724 (e.g., a second source electrode 723 and a second drain electrode 724), third source/drain electrodes 725 and 726 (e.g., a third source electrode 725 and a third drain electrode 726), fourth source/drain electrodes 731 and 732 (e.g., a fourth source electrode 731 and a fourth drain electrode 732), and fifth source/drain electrodes 733 and 734 (e.g., a fifth source electrode 733 and a fifth drain electrode 734) may be provided on the second insulating layer INS2. The first to fifth source/drain electrodes 721, 722, 723, 724, 725, 726, 731, 732, 733, and 734 may be connected to the corresponding first to fifth active patterns ACT11, ACT12, ACT13, ACT21, and ACT22 through respective contact holes.

The first to fifth source/drain electrodes 721, 722, 723, 724, 725, 726, 731, 732, 733, and 734 may include metal. The first to fifth source/drain electrodes 721, 722, 723, 724, 725, 726, 731, 732, 733, and 734 may include material having high conductivity. For example, the first to fifth source/drain electrodes 721, 722, 723, 724, 725, 726, 731, 732, 733, and 734 may include conductive material including molybdenum (Mo), aluminum (Al), copper (Cu), titanium (Ti), and the like. The first to fifth source/drain electrodes 721, 722, 723, 724, 725, 726, 731, 732, 733, and 734 may have a multilayer structure or a single-layer structure including the foregoing material. For example, the first to fifth source/drain electrodes 721, 722, 723, 724, 725, 726, 731, 732, 733, and 734 may have a multilayer structure Ti/Al/Ti.

A third insulating layer INS3 may be provided on the first to fifth source/drain electrodes 721, 722, 723, 724, 725, 726, 731, 732, 733, and 734. For example, the third insulating layer INS3 may be formed of an organic insulating layer including organic material. The third insulating layer INS3 may include organic insulating material, e.g., a general-purpose polymer such as polymethylmethacrylate or polystyrene, polymer derivative including a phenolic group, an acrylic polymer, an imide-based polymer, aryl ether-based polymer, amide-based polymer, fluorinate polymer, p-xylene-based polymer, vinyl alcohol-based polymer, and a blend thereof. The third insulating layer INS3 may function to planarize an area on the first to fifth source/drain electrodes 721, 722, 723, 724, 725, 726, 731, 732, 733, and 734.

Connection patterns CNP1 and CNP2 may be provided on the third insulating layer INS3. The first connection pattern CNP1 may be connected to the first drain electrode 722 through a contact hole that passes through the third insulating layer INS3. The second connection pattern CNP2 may be connected to the fifth drain electrode 734 (or the fifth source electrode 733) through a contact hole that passes through the third insulating layer INS3.

The connection patterns CNP1 and CNP2 may be made of at least one of metals such as gold (Au), silver (Ag), aluminum (Al), molybdenum (Mo), chrome (Cr), titanium (Ti), nickel (Ni), neodymium (Nd), copper (Cu), or an alloy of the metals.

A fourth insulating layer INS4 may be disposed on the connection patterns CNP1 and CNP2. The fourth insulating layer INS4 may be formed of an organic insulating layer including organic material. The fourth insulating layer INS4 may include organic insulating material, for example, a general-purpose polymer such as polymethylmethacrylate or polystyrene, polymer derivative including a phenolic group, an acrylic polymer, an imide-based polymer, aryl ether-based polymer, amide-based polymer, fluorinate polymer, p-xylene-based polymer, vinyl alcohol-based polymer, and a blend thereof. The fourth insulating layer INS4 may function to planarize an area on the connection patterns CNP1 and CNP2.

A pixel layer including a first pixel electrode PEL1, a first sensor electrode SEL1, and a "pixel bank layer" ("bank layer") BK (or a "pixel defining layer") may be provided on the fourth insulating layer INS4.

The pixel layer may include a light emitting element LD connected to a pixel driving circuit (e.g., the pixel driving circuit PXC of FIG. 6), and a light receiving element LRD connected to a sensor circuit (e.g., a photo sensor driving circuit PSC of FIG. 6).

In an embodiment, the light emitting element LD may include a first pixel electrode PEL1, a first hole transport layer HTL1, a light emitting layer EML, an electron transport layer ETL, and a second pixel electrode PEL2. In an embodiment, the light receiving element LRD may include a first sensor electrode SEL1, a second hole transport layer HTL2, a light receiving layer LRL, an electron transport layer ETL, and a second sensor electrode SEL2.

In an embodiment, the first pixel electrode PEL1 and the first sensor electrode SEL1 may include a metal layer made of silver (Ag), magnesium (Mg), aluminum (Al), platinum (Pt), palladium (Pd), gold (Au), nickel (Ni), neodymium (Nd), iridium (Ir), chrome (Cr), or an alloy thereof, and/or indium tin oxide (ITO), indium zinc oxide (IZO), zinc oxide (ZnO), indium tin zinc oxide (ITZO), or the like. The first pixel electrode PEL1 may be connected to the first drain electrode 722 through a contact hole. The first sensor electrode SEL1 may be connected to the fifth drain electrode 734 through a contact hole.

The first pixel electrode PEL1 and the second sensor electrode SEL1 may be formed through the same process by a patterning method using a mask.

The bank layer BK may define a light emitting area and a light receiving area by including openings respectively corresponding to each of these areas. The bank layer BK may be provided on the fourth insulating layer INS4 on which the first pixel electrode PEL1 and the first sensor electrode SEL1 are formed. The bank layer BK may be formed of an organic insulating layer including organic material. The organic material may include acryl resin, epoxy resin, phenolic resin, polyamide resin, polyimide resin, or the like.

Furthermore, the bank layer BK may include light absorbing material (included inherently or as an applied layer) so that the bank layer BK can absorb incident light. For example, the bank layer BK may include a carbon-based black pigment. In other examples, the bank layer BK includes opaque metal such as chrome (Cr), molybdenum (Mo), an alloy (MoTi) of molybdenum and titanium, tungsten (W), vanadium (V), niobium (Nb), tantalum (Ta), manganese (Mn), cobalt (Co), and/or nickel (Ni), each having high light absorptivity.

The first hole transport layer HTL1 may be provided on an upper surface of the first pixel electrode PEL1 that is exposed from the bank layer BK. The second hole transport layer HTL2 may be provided on an exposed upper surface of the first sensor electrode SEL1. Holes may move to the light emitting layer EML through the first hole transport layer HTL1. Holes may move to the light receiving layer LRL through the second hole transport layer HTL2.

The first hole transport layer HTL1 and the second hole transport layer HTL2 may be identical to or different from each other, depending on the materials of the light emitting layer EML and the light receiving layer LRL.

The light emitting layer EML may be provided on the first hole transport layer HTL1. In an embodiment, the light emitting layer EML may include an organic light emitting layer. Depending on the organic material included in the light emitting layer EML, the light emitting layer EML may emit light in a red wavelength band, may emit light in a green wavelength band, or may emit light in a blue wavelength band.

In an embodiment, an electron blocking layer may be provided on the second hole transport layer HTL2 in the light receiving area. The electron blocking layer may prevent a charge of the light receiving layer LRL from moving to the second hole transport layer HTL2. In an embodiment, the electron blocking layer may be omitted.

The light receiving layer LRL may be disposed on the second hole transport layer HTL2. The light receiving layer LRL may emit electrons in response to light in a specific wavelength band. Thereby, the intensity ("quantity") of light may be sensed.

In an embodiment, the light receiving layer LRL may include low-molecular organic material. For example, the light receiving layer LRL may be formed of a phthalocyanine compound including one or more metals selected from the group consisting of copper (Cu), iron (Fe), nickel (Ni), cobalt (Co), manganese (Mn), aluminum (Al), palladium (Pd), tin (Sn), indium (In), lead (Pb), titanium (Ti), rubidium (Rb), vanadium (V), gallium (Ga), terbium (Tb), cerium (Ce), lanthanum (La), and zinc (Zn).

The low-molecular organic material included in the light receiving layer LRL may include a phthalocyanine compound including one or more metals selected from the group consisting of copper (Cu), iron (Fe), nickel (Ni), cobalt (Co), manganese (Mn), aluminum (Al), palladium (Pd), tin (Sn), indium (In), lead (Pb), titanium (Ti), rubidium (Rb), vanadium (V), gallium (Ga), terbium (Tb), cerium (Ce), lanthanum (La), and zinc (Zn).

The light receiving layer LRL may have a bi-layer structure. The light receiving layer LRL may include a layer including a phthalocyanine compound, and a layer including C60.

The light receiving layer LRL may include a single mixing layer formed by mixing the phthalocyanine compound and C60.

However, the foregoing is only for illustrative purposes, and the light receiving layer LRL may include a high-molecular organic layer.

In an embodiment, a light detection band of the light receiving element LRD may be determined depending on selection of metal components of the phthalocyanine compound included in the light receiving layer LRL. For example, in the case of a phthalocyanine compound including copper, a visible light wavelength in a band ranging from approximately 600 nm (nanometer) to approximately 800 nm may be absorbed. In the case of a phthalocyanine compound including tin (Sn), a near-infrared light wavelength in a band ranging from approximately 800 nm to approximately 1000 nm may be absorbed.

A photo sensor capable of detecting a wavelength of a band desired by the user can be implemented according to selection of metals included in the phthalocyanine compound. For example, the light receiving layer LRL may be formed to selectively absorb light in the red wavelength band, light in the green wavelength band, or light in the blue wavelength band.

In an embodiment, the surface area of the light receiving area may be less than that of the light emitting area. The surface area of the light receiving area may correspond to a width d of an opening BMH to be described below.

The second pixel electrode PEL2 and the second sensor electrode SEL2 may be provided on the electron transport layer ETL. The second pixel electrode PEL2 and the second sensor electrode SEL2 may be implemented as a common electrode CD which is integrally formed in the display area. The second power voltage VSS may be supplied to the second pixel electrode PEL2 and the second sensor electrode SEL2.

The common electrode CD may be formed of a metal layer formed of material such as silver (Ag), magnesium (Mg), aluminum (Al), platinum (Pt), palladium (Pd), gold (Au), nickel (Ni), neodymium (Nd), iridium (Ir), chrome (Cr), or an alloy thereof, and/or a transparent conductive layer formed of material such as ITO, IZO, ZnO, or ITZO. In an embodiment, the common electrode CD may have a multilayer structure having two or more layers including a thin metal layer. For example, the common electrode CD may have a triple-layer structure including ITO/Ag/ITO.

An encapsulation layer TFE may be provided on the common electrode CD including the second pixel electrode PEL2 and the second sensor electrode SEL2. The encapsulation layer TFE may have a single-layer structure, or may have a multilayer structure. In an embodiment, the encapsulation layer TFE may have a stacked structure formed by successively depositing inorganic material, organic material, and inorganic material. An uppermost layer of the encapsulation layer TFE may be formed of inorganic material.

In embodiments of the present disclosure, a touch screen panel TSP may be provided on the encapsulation layer TFE. The touch screen panel TSP may include a touch electrode formed to sense a touch of the user. The touch screen panel TSP may be implemented by a self-capacitive method, or may be implemented by a mutual-capacitive method.

In embodiments of the present disclosure, the touch screen panel TSP may be an in-cell type panel, which is integrally formed during a process of forming the display panel 210 (refer to FIGS. 2 and 3). The touch screen panel TSP may be an on-cell type panel (or referred also to as an add-on type panel), which is formed separately from the display panel 210 and then attached to the display panel 210. Although for convenience of explanation the case where the touch screen panel TSP is an in-cell type panel will be described by way of example, embodiments of the present disclosure are not limited thereto.

A display device in accordance with embodiments of the present disclosure may include a pressure sensor (not illustrated) configured to sense a touch pressure. The pressure sensor may be formed integrally with the touch screen panel TSP, but may be formed as a separate component from the touch screen panel TSP.

In embodiments of the present disclosure, the pressure sensor may be an in-cell type sensor, which is integrally formed during a process of forming the display panel 210 (refer to FIGS. 2 and 3). The pressure sensor may be an on-cell type sensor (or an add-on type sensor), which is formed separately from the display panel 210 and then attached to the display panel 210. In the case where an add-on type pressure sensor is attached to the display panel 210, the pressure sensor may be attached to a lower surface of the base layer BL.

Although the case where the display device in accordance with embodiments of the present disclosure includes an add-on type pressure sensor is described herein by way of example, other embodiments may omit the pressure sensor or additionally or alternatively include other types of sensors.

A black matrix layer BM may be disposed on the touch screen panel TSP. In an embodiment, a color filter layer CF may be disposed on the black matrix layer BM. Depending on the design of the pixel layer, the color filter layer CF may be omitted. A cover glass layer CG may be disposed in an uppermost layer of the display panel (e.g., a layer over the color filter layer CF).

At least a portion of the black matrix layer BM may be disposed to overlap the bank layer BK. In terms of the pixels, the black matrix layer BM may function to distinguish a plurality of pixels from each other. The black matrix layer BM may separate the pixels from each other so that light emitted from the pixels can be prevented from being mixed with each other. In terms of the photo sensors, the black matrix layer BM may function as an optical system, which may gather light.

For example, referring to FIG. 7, the black matrix layer BM may include an opening BMH. At least a portion of the black matrix layer BM may be removed to form the opening BMH. The opening BMH may be located to overlap the light receiving element LRD. Due to the opening BMH, the black matrix layer BM may function as an optical system.

Light incident toward the light receiving element LRD (e.g., reflective light emitted from the light emitting element LD and reflected by an external object or the like) may be adjusted in quantity by the optical system (e.g., a width d of the optical system) formed by the black matrix layer BM. If the width d of the opening BMH is small, the quantity of light incident on the light receiving element LRD is relatively small. Conversely, if the width d of the opening BMH is large, the quantity of light that is incident on the light receiving element LRD is relatively large.

As the width d of the opening BMH is reduced, the focal distance is increased in terms of the optical system. The characteristic in which the focal distance is increased may be beneficial to generation of an image having a fine pattern, as in the case where a fingerprint image is acquired in the electronic device. The width d of the opening BMH may be, for example, approximately 6 μm (micrometer).

However, as the width d of the opening BMH is reduced, the absolute quantity of light that is incident on the light receiving element LRD is reduced. The foregoing characteristic may impede the electronic device from performing an operation of sensing a change in the quantity of light and generating data about biometric signals (e.g., blood pressure, a heart rate, oxygen saturation, and the like).

In the electronic device in accordance with embodiments of the present disclosure, a biometric authentication mode and a biometric signal measurement mode may differ from each other in resolution at which the photo sensors sense images. The mode for biometric authentication may include a fingerprint authentication mode. Other biometric examples in the biometric authentication mode may include facial recognition and/or iris recognition. The biometric signal measurement mode may include, for example, a heartbeat measuring mode.

In embodiments of the present disclosure, a plurality of pixel rows may be sensed on a row basis, in the fingerprint authentication mode. Thereby, an image having the first sensing resolution may be generated.

In embodiments of the present disclosure, in the heartbeat measuring mode, two or more pixel rows among the plurality of pixel rows may be sensed together (e.g., sensed integrally). In this case, although the sensing resolution is reduced compared to the case where each pixel row is sensed, the quantity of light (or a change thereof) acquired through a single sensing operation may be greater than that for the case where each pixel row is sensed.

The electronic device in accordance with embodiments of the present disclosure may generate an image having the second sensing resolution. The electronic device in accordance with embodiments of the present disclosure may generate video data (data for a moving image) having the second sensing resolution, including two or more images having the second sensing resolution. In the electronic device in accordance with embodiments of the present disclosure, a change in the quantity of light based on a video having the second sensing resolution may be detected, so that change trend information of the biometric signal (e.g., a heart rate or the like) of the user of the electronic device can be generated. It is noted here that in each or either one of the high resolution and low resolution modes, a result of the still image or video data, but not the image or video, may be displayed, recorded or audibly presented, etc. For instance, a positive comparison of the still image data in the high resolution mode with pre-stored fingerprint data may automatically unlock the electronic device for the user. In the low resolution mode, a biometric parameter result based on the captured video data may be displayed in heartbeats/second, blood pressure, etc.

In the electronic device in accordance with embodiments of the present disclosure, the sensing resolution may be controlled to vary depending on the mode. The electronic device in accordance with embodiments of the present disclosure may generate a still image having the first sensing resolution and a video having the second sensing resolution with one photo sensor. In the electronic device in accordance with embodiments of the present disclosure, the width d of the opening BMH that is located to overlap the light receiving sensor LRD may be uniform (e.g., identical, substantially identical, or even).

In accordance with embodiments of the present disclosure, a photo sensor for generating an image having the first sensing resolution and a photo sensor for generating an image having the second sensing resolution may be integrated. In other words, both a sensing operation for biometric authentication and a sensing operation for generating biometric signal data may be performed by one photo sensor. Thus, overall circuit complexity to achieve both functions may be reduced relative to conventional electronic devices through use of shared photo sensors and associated circuit elements. Moreover, when adjacent rows each include a photo sensor, during the low resolution mode, signal values from the photo sensors of adjacent rows may be summed, and the summed value may be analyzed by the processor instead of the individual signal values. Thus, as compared to a method utilizing row by row analysis of photo sensor signals (a high resolution method), less processing power may be consumed in the low resolution mode, with minimal or negligible impact on measurement accuracy for the biometric parameter.

Figure 8:
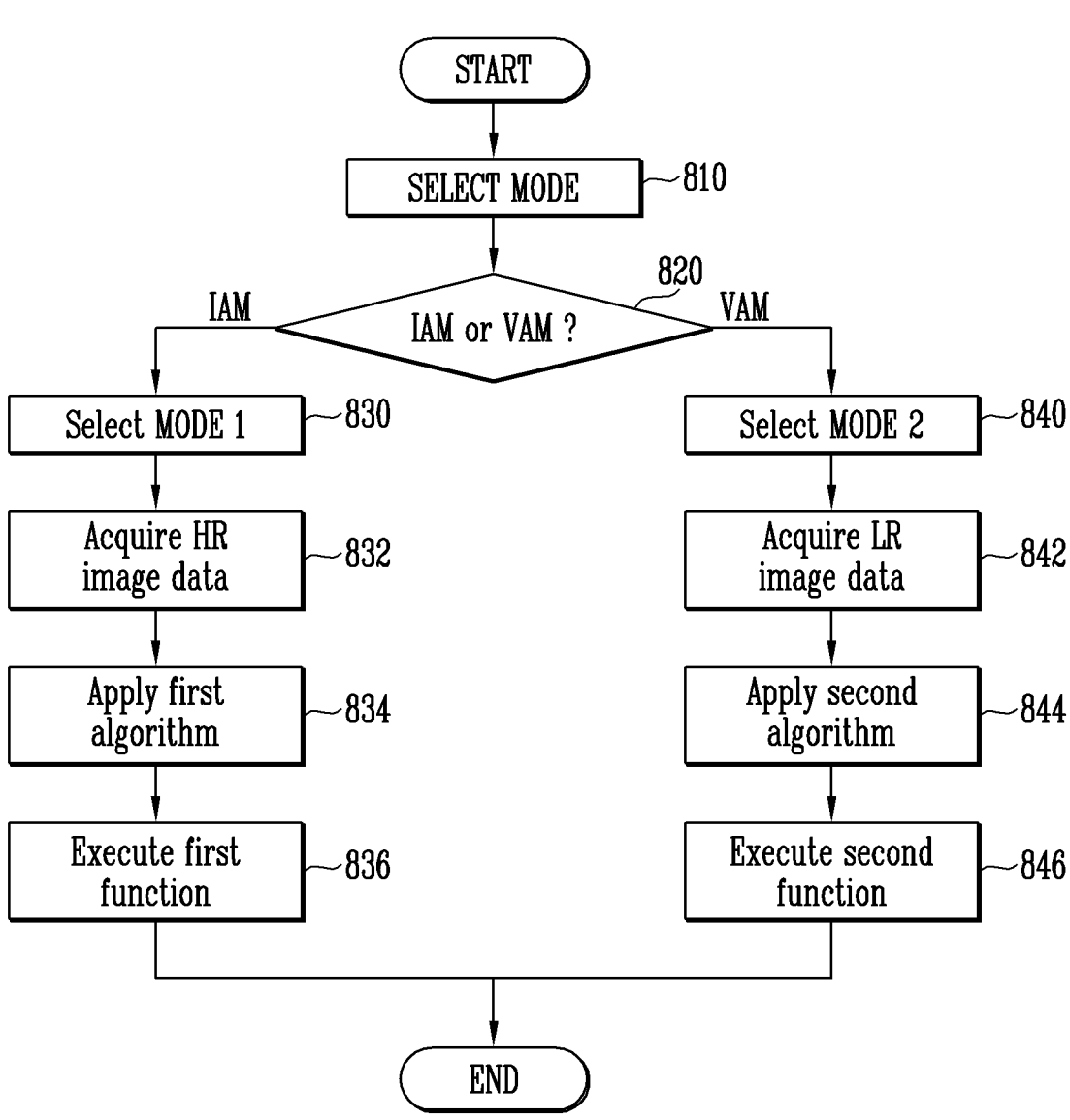
FIG. 8 is a flowchart illustrating a method of driving an electronic device in accordance with embodiments of the present disclosure.

FIG. 8 is a flowchart illustrating a method of driving the electronic device in accordance with embodiments of the present disclosure. The method may be executed by the processor 130 (shown in FIG. 1) of the electronic device.

At operation 810, a mode may be selected, e.g., by displaying an icon on the electronic device's display area and detecting a touch input upon the icon for instructing software (e.g., an application of a smart phone or the like) to be executed is displayed on a screen (e.g., a display area) of the electronic device.

At operation 820, a detected selection may be made of one of an image acquiring mode IAM (correspond to a first mode MODE 1) and a video acquiring mode VAM (correspond to a second mode MODE 2). The image acquiring mode IAM may be a mode set to acquire an image having the first sensing resolution. The video acquiring mode VAM may be a mode set to acquire a video having the second sensing resolution (or an image having the second sensing resolution). One of the image acquiring mode IAM and the video acquiring mode VAM may be selected by input from the user of the electronic device, a request for another program to be executed in the electronic device, or the like.

The image acquiring mode IAM may include, for example, a biometric authentication mode (e.g., a fingerprint authentication mode).

The video acquiring mode VAM may include, for example, a mode in which a biometric signal (e.g., blood pressure, a heart rate, oxygen saturation, or the like) is measured.

When the first mode MODE 1 is selected at operation 830, operation 832 of acquiring (or generating) an image having the first sensing resolution is performed. The image having the first sensing resolution may refer to an image having a relatively high resolution. Operation 834 of applying a first algorithm may follow. The first algorithm may include, an algorithm for removing (or reducing) noise from the image, an algorithm for enhancing uniformity of the acquired image, and an algorithm for de-blurring the image to make a blurred portion of the image clear. The first algorithm may include an algorithm for detecting minutiae from a generated fingerprint image. Additionally or alternatively, the first algorithm may include an algorithm known to those skilled in the art related to the biometric authentication. The first algorithm may be obtained by learning (e.g., machine learning) in the electronic device in accordance with embodiments of the present disclosure, or may be obtained by executing an already learned algorithm stored in a memory (e.g., the memory 150 of FIG. 1).

Operation 836 of executing a first function may follow. The first function may include, an authentication function. Executing the first function may involve comparing image data (e.g., image data having the first sensing resolution) acquired by applying the first algorithm with pre-stored reference data (e.g., pre-registered biometric information of the user of the electronic device). For example, the first function may include a function of determining whether the degree of similarity is a preset threshold value or more as a result of comparison of the image data having the first sensing resolution and the reference data.

In the electronic device, a touch for biometric authentication may be inputted to at least a partial area of the display area AA (refer to FIG. 2). Here, at least the partial area may be or include an arbitrary area, a preset area, or the like of the display area AA. For example, the user of the electronic device may bring his/her finger into contact with an arbitrary area of the display area AA so that the fingerprint authentication can be performed. When the user's finger contacts the area, photosensors in the region of the contact may detect reflections from light emitted by pixels in the region of the contact to generate fingerprint image data.

When the video acquiring mode VAM is selected at operation 820, operation 840 of selecting the second mode MODE 2 may be performed. This may involve operation 842 of acquiring an image having the second sensing resolution. The image having the second sensing resolution may refer to an image having a relatively low resolution.

Operation 844 of applying a second algorithm may follow. The second algorithm may include, for example, an algorithm for removing (or filtering) noise from an image, an algorithm for time-frequency analysis, and the like. In addition, the second algorithm may include an algorithm known to those skilled in the art related to biometric signal measurement. The second algorithm may be obtained by learning (e.g., machine learning) in the electronic device in accordance with embodiments of the present disclosure, or may be obtained by storing an already learned algorithm in the memory (e.g., the memory 150 of FIG. 1).

Operation 846 of executing a second function may be performed thereafter. For example, the second function may include a function of measuring a biometric signal.

For example, the electronic device may measure at least one of the blood pressure, the heart rate, and the oxygen saturation of the user of the electronic device in at least a partial area of the display area AA (shown in FIG. 2). Here, at least the partial area may include a preset area, or an arbitrary area (e.g., an area which is determined by a touch sensor that a touch has been inputted thereto, or an area where the quantity of light sensed by the photo sensor is a threshold value or less) in the display area AA. For example, the user of the electronic device may bring his/her finger into contact with an arbitrary area of the display area AA so that an operation of measuring of a biometric signal can be performed. The area of contact may be determined by touch sensors of the electronic device. The arbitrary area may be an area overlapping the area discussed above for the fingerprint measurement, such that the low resolution and high resolution measurements may utilize shared pixels in the contact area to illuminate the object, and shared photo sensors in the contact area to receive reflected light from the illuminated object.

For example, the electronic device may display, in a remaining partial area of the display area AA (refer to FIG. 2), an image (or a video) indicating a measured biometric signal, or a trend of change of the measured biometric signal as a function of time.

The electronic device in accordance with embodiments of the present disclosure may store the measured biometric signal in a memory (e.g., the non-volatile memory 154 of FIG. 1).

The second function may further include a function of calibrating the biometric signal measured by the electronic device. For example, the electronic device in accordance with embodiments of the present disclosure may receive a biometric signal measured by another medical apparatus (e.g., a blood pressure gauge, or the like), and may calibrate, based on the corresponding value, the biometric signal measured by the electronic device. The second algorithm may be adaptively corrected by the calibration.

In the electronic device in according with an embodiment of the present disclosure, an area which receives a touch for biometric authentication in the case where the first mode MODE 1 is selected and an area which receives a touch to measure a biometric signal in the case where the second mode MODE 2 is selected may overlap each other (or may be identical or substantially identical to each other).

Figure 9:
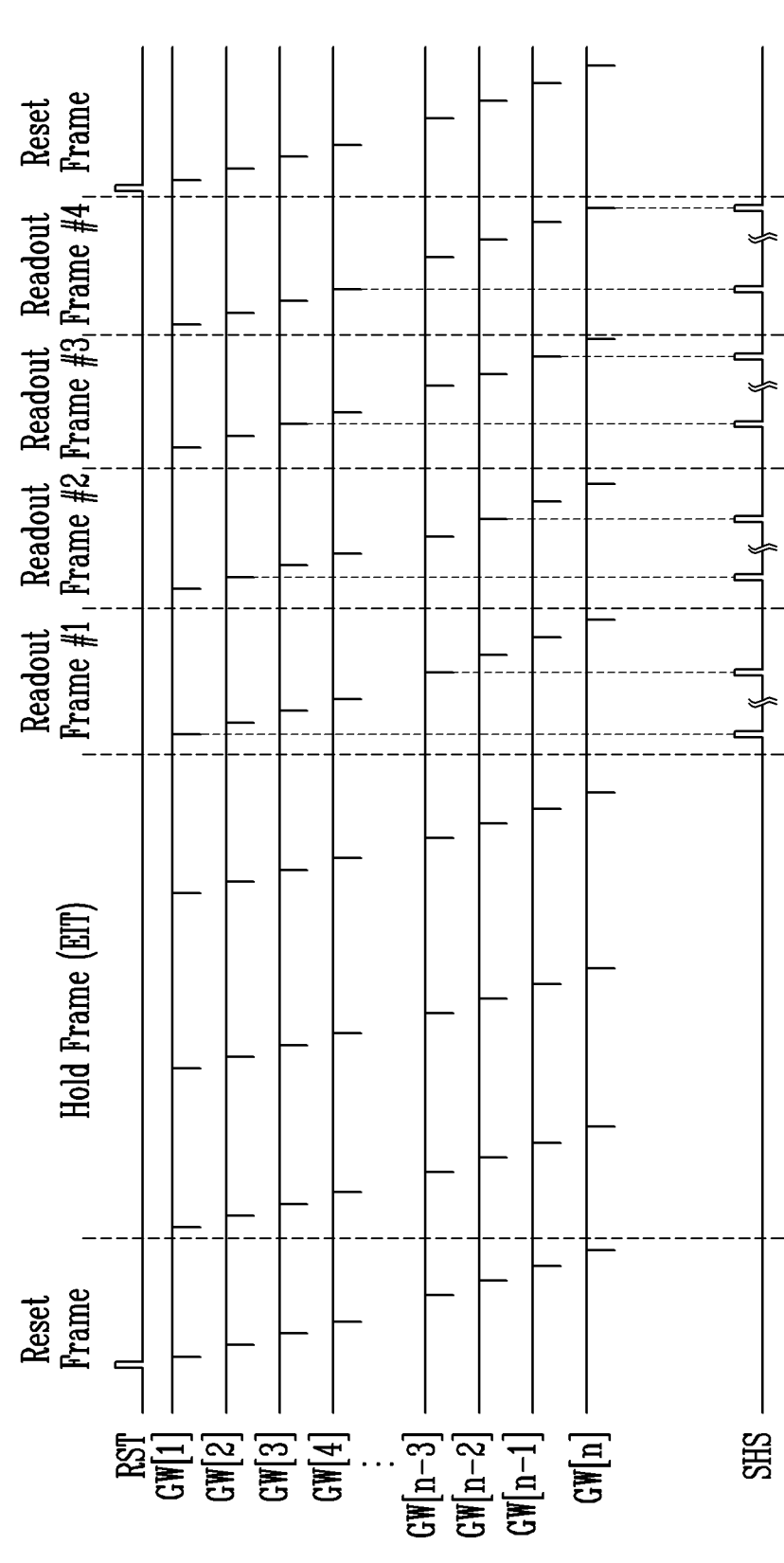
FIG. 9 is a timing diagram of the display device that senses a photo sensor at a first sensing resolution in the case where a first mode is selected, in accordance with embodiments of the present disclosure.

FIG. 9 illustrates a timing diagram of the display device that senses a photo sensor at the first sensing resolution in the case where the first mode MODE 1 is selected, in accordance with embodiments of the present disclosure.

Referring to FIG. 9, there is illustrated a timing diagram of a reset signal RST, first scan signals GW[1] to GW[n], and a first sampling signal SHS (referred also to as a sample-and-hold signal SHS).

Referring to FIGS. 3 and 9, the reset circuit 360 may output the reset signal RST. The scan driving circuit 320 may output the first scan signals GW[1] to GW[n]. The first sampling signal SHS may be included in the readout circuit control signal RCS. The timing controller 340 may output the first sampling signal SHS. The readout circuit 350 may receive the first sampling signal SHS so that a timing at which the photo sensor PHS is sensed and/or a length of a period during which the photo sensor PHS is sensed can be controlled.

If the first mode MODE 1 is selected, a reset frame may start. In the reset frame, the reset circuit 360 (refer to FIG. 3) may output a reset signal RST. The reset signal RST may be outputted before the first scan signals GW[1] to GW[n]. Thereby, the voltage of the sensing line RXk (referring to FIG. 6) may be reset (or initialized).

Referring to FIGS. 6 and 9 together, if the reset signal RST is inputted and the third sensor transistor M3a is thus turned on, a third power voltage VRST is applied to the fifth node N5. The first sensor transistor M1 may be turned on in response to the third power voltage VRST applied to the fifth node N5. The second sensor transistor M2 may be turned on in response to a first scan signal GW[i] of a turn-on level. If the first sensor transistor M1 and the second sensor transistor M2 are turned on, the voltage level of the sensing line RXk may be initialized to the fourth power voltage VCOM.

After the reset frame, an exposure integration time (EIT) may proceed. The EIT may include one or more hold frames. The EIT may correspond to a period during which the photo sensor receives light (e.g., a period during which light is received after the reset frame before a readout frame).

Referring to FIGS. 6 and 9 together, during the EIT (or one or more hold frame periods), the photo sensor PHS may receive light, so that current can flow through the light receiving element LRD. The first mode MODE 1 may be a mode for biometric authentication. In the first mode MODE 1, the length of the EIT may be set to be long enough for the magnitude of current flowing through the light receiving element LRD to be relatively uniform (or enough to converge to a certain value). For example, the length of the EIT may be approximately 100 ms (millisecond) (or approximately twelve frame periods based on a scan rate of 120 Hz), embodiments of the present disclosure are limited thereto. Thereby, each of the plurality of photo sensors PHS may reflect a minute difference in the light receiving amount.

After the EIT, one or more readout frames may proceed. In the readout frame, a first sampling signal SHS of a turn-on level may be applied to the readout circuit 350 (refer to FIG. 3).

In the readout frame, a plurality of photo sensors may be sensed.

In the selected first mode MODE 1, the first sampling signal SHS of a turn-on level may be applied during one horizontal period.

In embodiments of the present disclosure, during one readout frame period, each of the plurality of photo sensors (e.g., all of the plurality of photo sensors) may be sensed. In embodiments of the present disclosure, the readout frame period may be divided into two or more readout frame periods, and in each readout frame, only a corresponding photo sensor among the plurality of photo sensors may be selectively sensed.

FIG. 9 illustrates an embodiment in which the readout frame period is divided into two or more readout frame periods, and during each readout frame, a corresponding photo sensor among the plurality of photo sensors is selectively sensed. In detail, in each of four readout frame periods Readout Frame #1 to Readout Frame #4, a corresponding photo sensor among the plurality of photo sensors is selectively sensed. However, embodiments of the present disclosure do not preclude an embodiment in which, during one readout frame, all of the plurality of photo sensors are sensed.

Referring to FIG. 9, in the first readout frame period Readout Frame #1 of the fourth readout frame periods Readout Frame #1 to Readout Frame #4, photo sensors located on first, fifth, . . . , n–3-th pixel rows (e.g., a pixel row of which a row number has a remainder of 1 when divided by 4) among the plurality of pixel rows may be sensed. In the second readout frame period Readout Frame #2, photo sensors located on second, sixth, . . . , n–2-th pixel rows (e.g., a pixel row of which a row number has a remainder of 2 when divided by 4) among the plurality of pixel rows may be sensed. In the third readout frame period Readout Frame #3, photo sensors located on third, seventh, . . . , n–1-th pixel rows (e.g., a pixel row of which a row number has a remainder of 3 when divided by 4) among the plurality of pixel rows may be sensed. In the fourth readout frame period Readout Frame #4, photo sensors located on fourth, eighth, . . . , n-th pixel rows (e.g., a pixel row of which a row number has a remainder of 0 when divided by 4) among the plurality of pixel rows may be sensed.

In accordance with embodiments of the present disclosure, in the first mode MODE1, a plurality of photo sensors may be sensed on a pixel row basis. Thereby, an image (e.g., a fingerprint image) having a relatively high sensing resolution (the first sensing resolution) may be generated.

Referring to FIG. 9, although it is illustrated that a reset frame Reset Frame starts immediately after the readout frame (e.g., the fourth readout frame Readout Frame #4), the first mode MODE 1 may be terminated without starting the reset frame Reset Frame after the readout frame.

Figure 10:
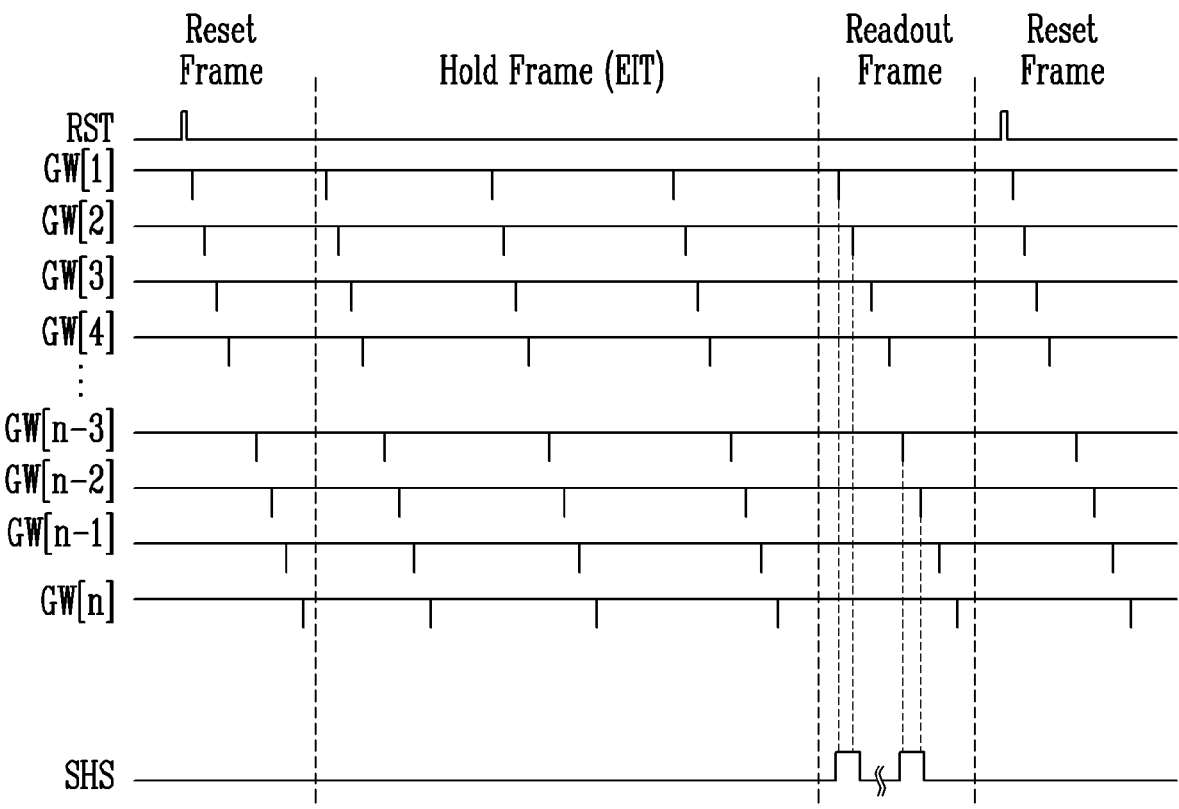
FIGS. 10 and 11 show examples of timing diagrams of the display device that senses a photo sensor at a second sensing resolution in the case where a second mode is selected, in accordance with embodiments of the present disclosure.
Figure 11:
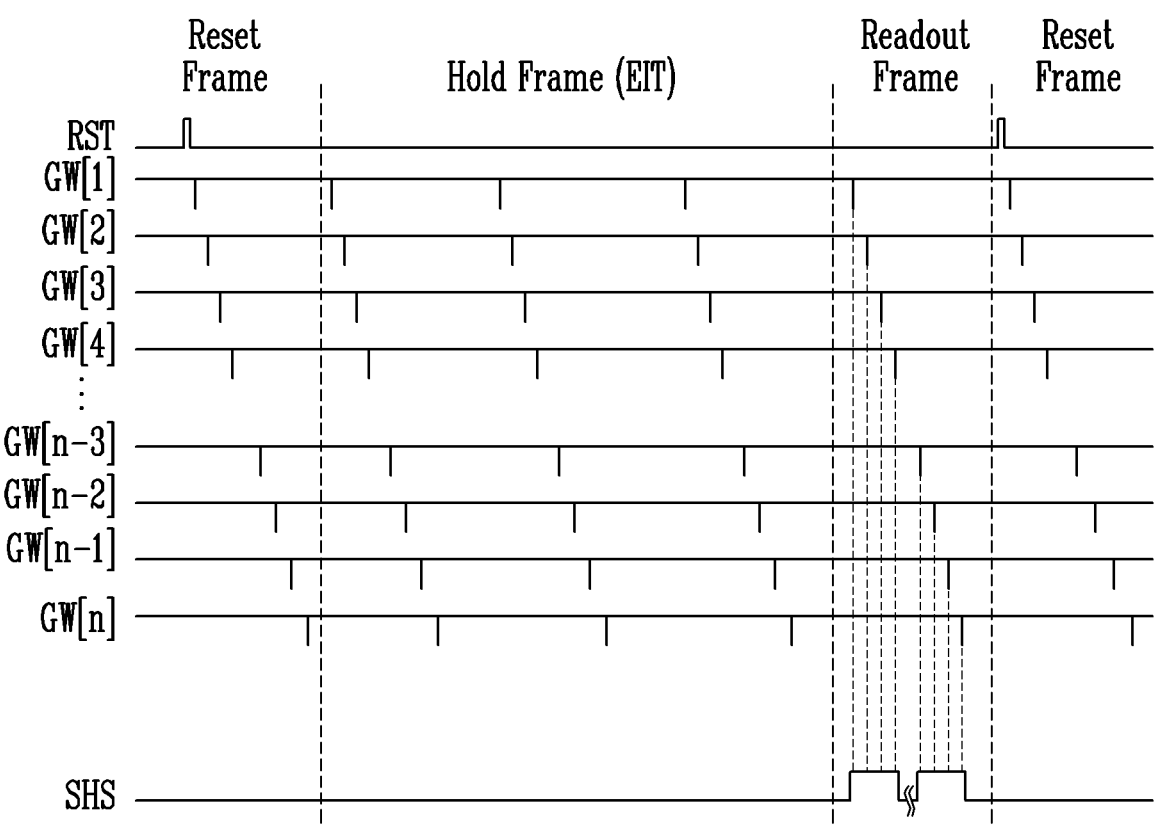

FIGS. 10 and 11 show examples of timing diagrams of the display device that senses a photo sensor at a second sensing resolution when the second mode MODE 2 is selected, in accordance with embodiments of the present disclosure.

FIGS. 10 and 11 illustrate timing diagrams of the reset signal RST, the plurality of first scan signals GW[1] to GW[n], and the first sampling signal SHS in the case where the second mode MODE 2 is selected.

The description of the reset frame is in common with that described with reference to FIG. 9; therefore, further explanation thereof will be omitted.

The length of the EIT in the selected second mode MODE 2 is shorter than the length of the EIT in the selected first mode MODE 1 (refer to FIG. 9). For example, the length of the EIT in the selected second mode MODE 2 may be 8.3 ms (or approximately one frame based on a scan rate of 120 Hz). The EIT in the selected second mode MODE2 may include two or more hold frames.

Referring to FIGS. 6, 10, and 11 together, the length of a period during which the photo sensor PHS in the selected second mode MODE 2 receives light (e.g., a period during which the photo sensor PHS receives light after the reset frame before the readout frame) may be relatively short. The electronic device 100 (refer to FIG. 1) in accordance with embodiments of the present disclosure may calculate the degree of change in the quantity of reflective light that is incident on the photo sensor PHS in the selected second mode MODE 2 as a function of time.

Referring to FIGS. 10 and 11, in the selected second mode MODE 2, a first sampling signal SHS of a turn-on level may be inputted to the readout circuit 350 (refer to FIG. 3) in the readout out frame period.

In the selected second mode MODE 2, the first sampling signal SHS of a turn-on level may be applied during at least two horizontal periods.

Referring to FIGS. 3 and 10 together, for example, during a period in which the first scan signal GW[1] is applied to the first pixel row and the first scan signal GW[2] is applied to the second pixel row, the first sampling signal SHS of a turn-on level may be inputted to the readout circuit 350. For example, during a period in which the first scan signal GW[n–3] is applied to the n–3-th pixel row and the first scan signal GW[n–2] is applied to the n–2-th pixel row GW[n–2], the first sampling signal SHS of a turn-on level may be inputted to the readout circuit 350.

Referring to FIGS. 3 and 11 together, for example, during a period in which the first scan signal GW[1] is applied to the first pixel row, the first scan signal GW[2] is applied to the second pixel row, the first scan signal GW[3] is applied to the third pixel row, and the fourth scan signal GW[4] is applied to the fourth pixel row, the first sampling signal SHS of a turn-on level may be inputted to the readout circuit 350. For example, during a period in which the first scan signal GW[n–3] is applied to the n–3-th pixel row, the n–2-th scan signal GW[n–2] is applied to the n–2-th pixel row, the first scan signal GW[n–1] is applied to the n–1-th pixel row, and the n-th scan signal GW[n] is applied to the n-th pixel row, the first sampling signal SHS of a turn-on level may be inputted to the readout circuit 350.

The electronic device 100 (refer to FIG. 1) in accordance with embodiments of the present disclosure may generate an image (or a video) based on a result of integrally sensing two or more pixel rows in the selected second mode MODE 2. In detail, an image (or a video) having a relatively low sensing resolution (the second sensing resolution) may be generated, based on a result of integrally sensing two or more pixel rows (e.g., photo sensors located on the two or more pixel rows).

Figure 12:
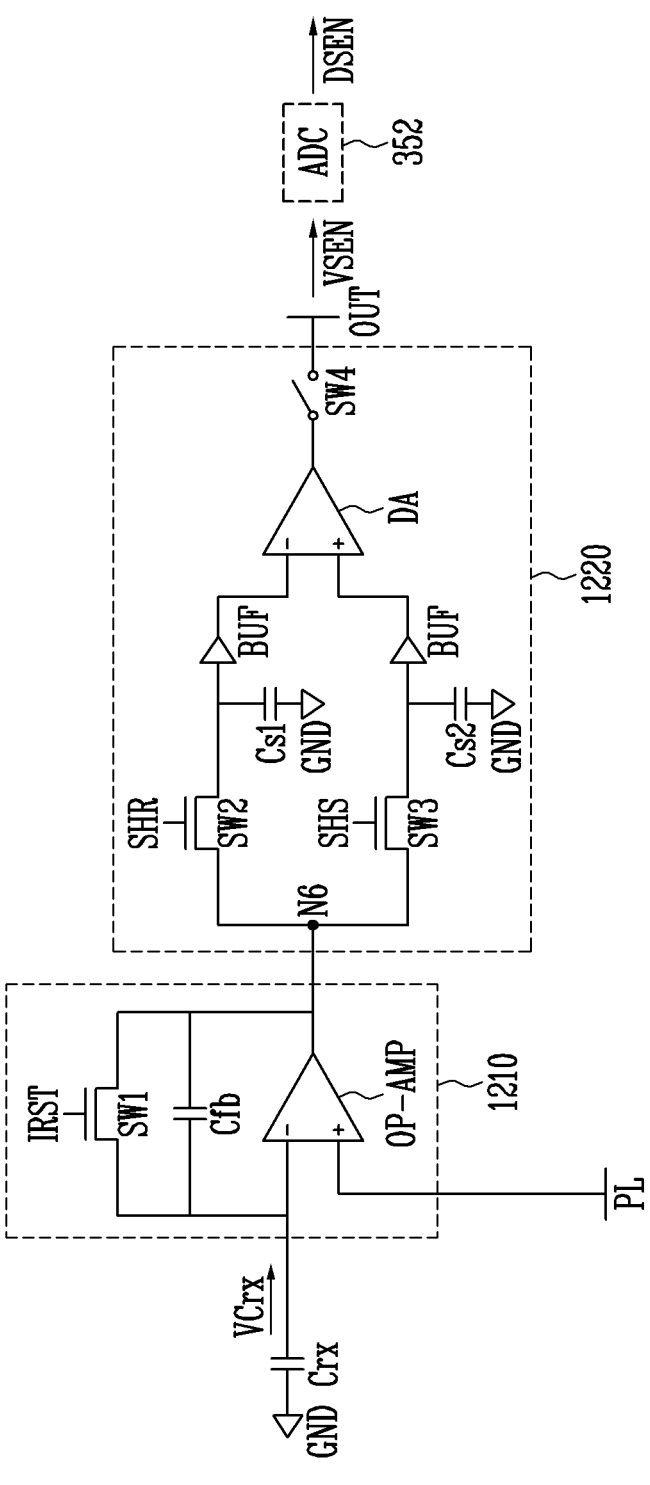
FIG. 12 illustrates an equivalent circuit of a readout circuit in accordance with embodiments of the present disclosure.

FIG. 12 illustrates an equivalent circuit of the readout circuit in accordance with embodiments of the present disclosure.

Referring to FIG. 12, the readout circuit in accordance with embodiments of the present disclosure may include an integrator 1210, and a sample-and-hold circuit 1220 (or referred also to as a correlated double sampling circuit).

The integrator 1210 may include an operational amplifier OP-AMP, a feedback capacitor Cfb, and a first switching element SW1. The first switching element SW1 may be controlled in operation timing by an integrator reset signal IRST.

The operational amplifier OP-AMP may include a first input terminal (e.g., (−) input terminal), a second input terminal (e.g., (+) input terminal), and an output terminal.

The first input terminal of the operational amplifier OP-AMP may be electrically connected to at least one of the plurality of sensing lines RX1 to RXo (shown in FIG. 3). To this end, a multiplexer may be further disposed between the first input terminal of the operational amplifier OP-AMP and the plurality of sensing lines. A voltage VCrx across a capacitor Crx, corresponding to a voltage of the sensing line may be applied to the first input terminal of the operational amplifier OP-AMP.

The second input terminal of the operational amplifier OP-AMP may be electrically connected to the power line PL. In some cases, the second input terminal of the operational amplifier OP-AMP may be connected to a ground GND.

The feedback capacitor Cfb may include a first side electrode electrically connected to the first input terminal of the operational amplifier OP-AMP, and a second side electrode electrically connected to the output terminal of the operational amplifier OP-AMP.

The first switching element SW1 may be configured to switch electrical connection between the first input terminal and the output terminal of the operational amplifier OP-AMP. If the first switching element SW1 is turned on, a charge stored in the feedback capacitor Cfb may be discharged, and the feedback capacitor Cfb may be reset.

The sample-and-hold circuit 1220 may include a second switching element SW2, a third switching element SW3, a first sampling capacitor Cs1, a second sampling capacitor Cs2, a differential amplifier DA, a fourth switching element SW4, and the like. The sample-and-hold circuit 1220 may include a sixth node N6 electrically connected to an output terminal of the integrator 1210 (e.g., the output terminal of the operational amplifier OP-AMP). In embodiments of the present disclosure, the sample-and-hold circuit 1220 may be configured to store a value acquired by sensing a signal value from the photo sensor, and output an analog voltage acquired by removing (or reducing) a noise component from the sensed value.

The second switching element SW2 may be configured to switch electrical connection between the sixth node N6 and the first sampling capacitor Cs1. The second switching element SW2 may be controlled in operation timing by a second sampling signal SHR.

The first sampling capacitor Cs1 may be configured to store a value corresponding to the noise component. The noise component may include, for example, a noise component which is basically present in the sensing line (e.g., RXk; refer to FIG. 6). The first sampling capacitor Cs1 may include a first side electrode electrically connected to the second switching element SW2, and a second side electrode electrically connected to a constant voltage source (or the ground GND).

The third switching element SW3 may be configured to switch electrical connection between the sixth node N6 and the second sampling capacitor Cs2. The third switching element SW3 may be controlled in operation timing by a first sampling signal SHS.

The second sampling capacitor Cs2 may be configured to store a value acquired by sensing the photo sensor signal including a noise component. The second sampling capacitor Cs2 may include a first side electrode electrically connected to the third switching element SW3, and a second side electrode electrically connected to a constant voltage source (or the ground GND).

The differential amplifier DA may include a first input terminal (e.g., (−) input terminal), a second input terminal (e.g., (+) input terminal), and an output terminal. The differential amplifier DA may be configured to amplify a signal (e.g., a voltage) corresponding to a difference between a signal (e.g., a voltage) inputted to the second input terminal and a signal (e.g., a voltage) inputted to the first input terminal, and output the amplified signal.

The first input terminal of the differential amplifier DA may be configured to receive a voltage applied from the first sampling capacitor Cs1. A buffer BUF may be further disposed between the first input terminal of the differential amplifier DA and the first sampling capacitor Cs1.

The second input terminal of the differential amplifier DA may be configured to receive a voltage applied from the second sampling capacitor Cs2. A buffer BUF may be further disposed between the second input terminal of the differential amplifier DA and the second sampling capacitor Cs2.

The fourth switching element SW4 may be configured to switch electrical connection between the output terminal of the differential amplifier DA and an input terminal OUT of the analog-to-digital converter (ADC) 352. If the fourth switching element SW4 is turned on, a sensing voltage VSEN corresponding to the light receiving amount of the photo sensor may be inputted to the analog-to-digital converter (ADC) 352.

The second switching element SW2 and the third switching element SW3 each may correspond to a switching element for sampling a signal. The fourth switching element SW4 may correspond to a switching element for holding a signal.

The analog-to-digital converter (ADC) 352 may convert the inputted sensing voltage VSEN to a digital value, and output the converted digital value DSEN.

Figure 13:
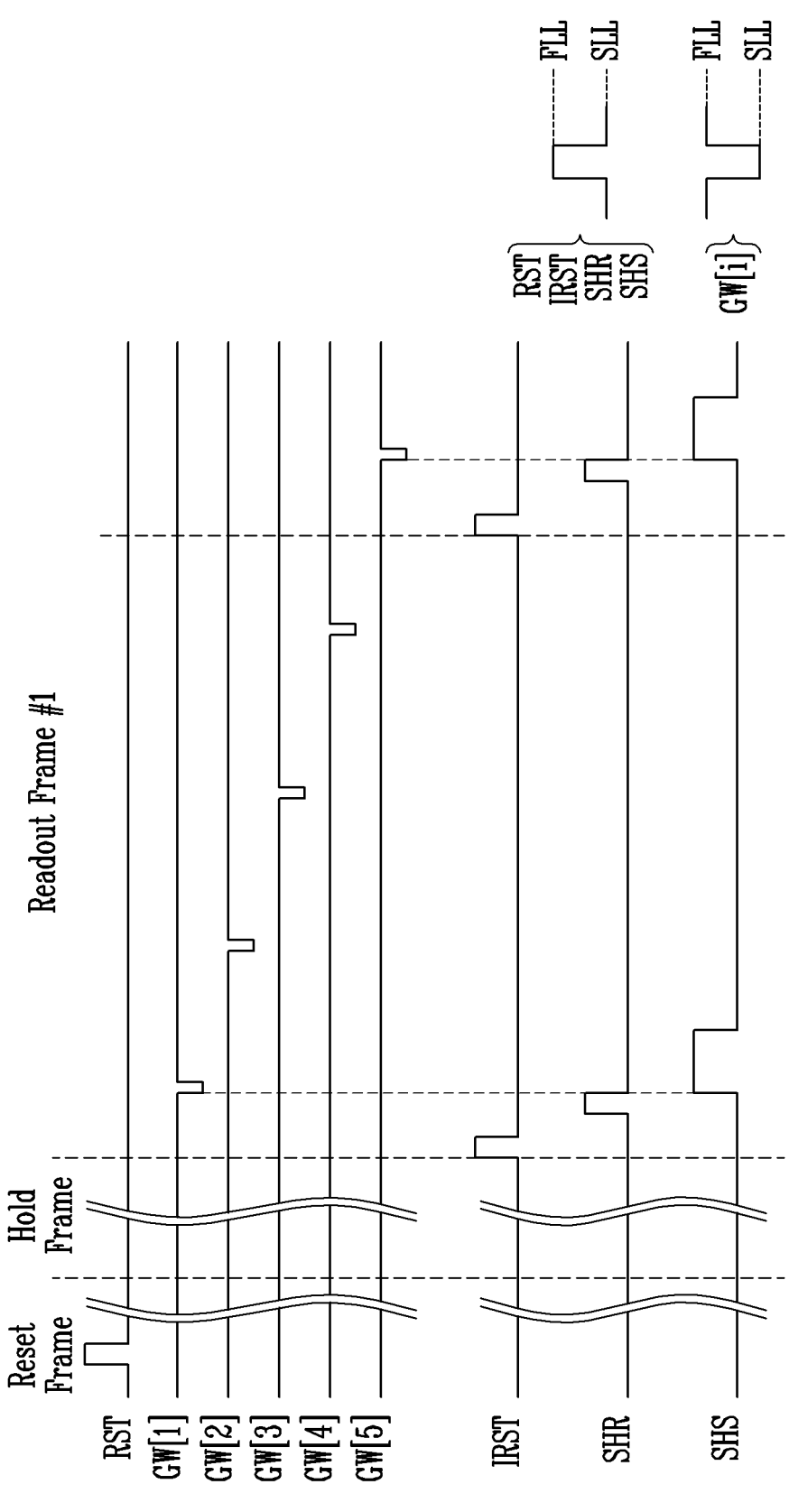
FIG. 13 illustrates an example of a first readout frame in the timing diagram illustrated in FIG. 9.

FIG. 13 illustrates an example of the first readout frame Readout Frame #1 in the timing diagram illustrated in FIG. 9.

For convenience of explanation, FIG. 13 illustrates only some scan signals GW[1] to GW[5] among n first scan signals GW[1] to GW[n].

Referring to FIG. 13, there are illustrated timings of a reset signal RST, a plurality of first scan signals GW[1] to GW[5], an integrator reset signal IRST, a first sampling signal SHS, and a second sampling signal SHR.

The integrator reset signal IRST and the first sampling signal SHS may be included in the above-mentioned readout circuit control signal RCS (refer to FIG. 3).

Here, it is assumed that each of the reset signal RST, the integrator reset signal IRST, the first sampling signal SHS, and the second sampling signal SHR has a first logic level FLL as a turn-on level, and has a second logic level SLL as a turn-off level. Furthermore, the following description will be made on the assumption that the first scan signal GW[i] has a second logic level SLL as a turn-on level, and has a first logic level FLL as a turn-off level. The first logic level FLL may be a high level, and the second logic level SLL may be a low level, but embodiments of the present disclosure are not limited thereto.

In the reset frame, the reset signal RST may have a turn-on level. In the reset frame, the plurality of first scan signals GW[1] to GW[5] may sequentially (or non-sequentially) have a turn-on level, and illustration thereof is omitted for convenience of explanation. In the reset frame, the integrator reset signal IRST, the first sampling signal SHS, and the second sampling signal SHR may have a turn-off level.

In the hold frame, the reset signal RST may have a turn-off level. In the hold frame, the plurality of first scan signals GW[1] to GW[5] may sequentially (or non-sequentially) have a turn-on level, and illustration thereof is omitted for convenience of explanation. In the hold frame, the integrator reset signal IRST, the first sampling signal SHS, and the second sampling signal SHR may have a turn-off level.

In the first readout frame (Readout Frame #1), the reset signal RST may have a turn-off level. In the first readout frame, the plurality of first scan signals GW[1] to GW[5] may sequentially (or non-sequentially) have a turn-on level.

If the first readout frame starts, the integrator reset signal IRST may have a turn-on level (or the voltage level of the integrator reset signal IRST may make a transition to a turn-on level). Thereafter, the voltage level of the integrator reset signal IRST may make a transition to a turn-off level. Thereby, the feedback capacitor Cfb (refer to FIG. 12) may be reset.

After the voltage level of the integrator reset signal IRST makes a transition to a turn-off level, the voltage level of the second sampling signal SHR may make a transition from a turn-off level to a turn-on level. While the second sampling signal SHR is applied at a turn-on level, a charge corresponding to noise may be stored in the first sampling capacitor Cs1 (refer to FIG. 12). The voltage level of the second sampling signal SHR may make a transition from a turn-on level to a turn-off level.

After the voltage level of the second sampling signal SHR makes a transition to a turn-off level, the voltage level of the first sampling signal SHR may make a transition from a turn-off level to a turn-on level.

A timing at which the voltage level of the first sampling signal SHS makes a transition from a turn-off level to a turn-on level may be the same as a timing at which the voltage level of the first scan signal (e.g., GW[1]) makes a transition from a turn-off level to a turn-on level. The timing at which the voltage level of the first sampling signal SHS makes a transition from a turn-off level to a turn-on level may be earlier than the timing at which the voltage level of the first scan signal (e.g., GW[1]) makes a transition from a turn-off level to a turn-on level.

The timing at which the voltage level of the first sampling signal SHS makes a transition from a turn-off level to a turn-on level may be the same as a timing at which the voltage level of the second sampling signal SHR makes a transition from a turn-on level to a turn-off level. In an embodiment, the timing at which the voltage level of the first sampling signal SHS makes a transition from a turn-off level to a turn-on level may be later than the timing at which the voltage level of the second sampling signal SHR makes a transition from a turn-on level to a turn-off level.

The voltage level of the first sampling signal SHS may make a transition to a turn-off level before the voltage level of a first scan signal (e.g., GW[2]) of a subsequent pixel row makes a transition from a turn-off level to a turn-on level.

A value corresponding to (or acquired by amplifying) a difference between a value sensed during a period in which the first sampling signal SHS has a turn-on level and a value sensed during a period in which the second sampling signal SHR has a turn-on level may be inputted to the analog-to-digital converter 352 (refer to FIGS. 3 and 12).

After the voltage level of the first sampling signal SHS makes a transition from a turn-on level to a turn-off level, the voltage level of the integrator reset signal IRST may make a transition from a turn-off level to a turn-on level. A voltage level change process of each of the second sampling signal SHR and the first sampling signal SHS is as described above.

Although the description with reference to FIG. 13 has been made based on the first readout frame (Readout Frame #1), the foregoing description may also be applied to the other readout frames (referring to FIG. 9, the second to fourth readout frames (Readout Frame #2 to Readout Frame #4)).

Figure 14:
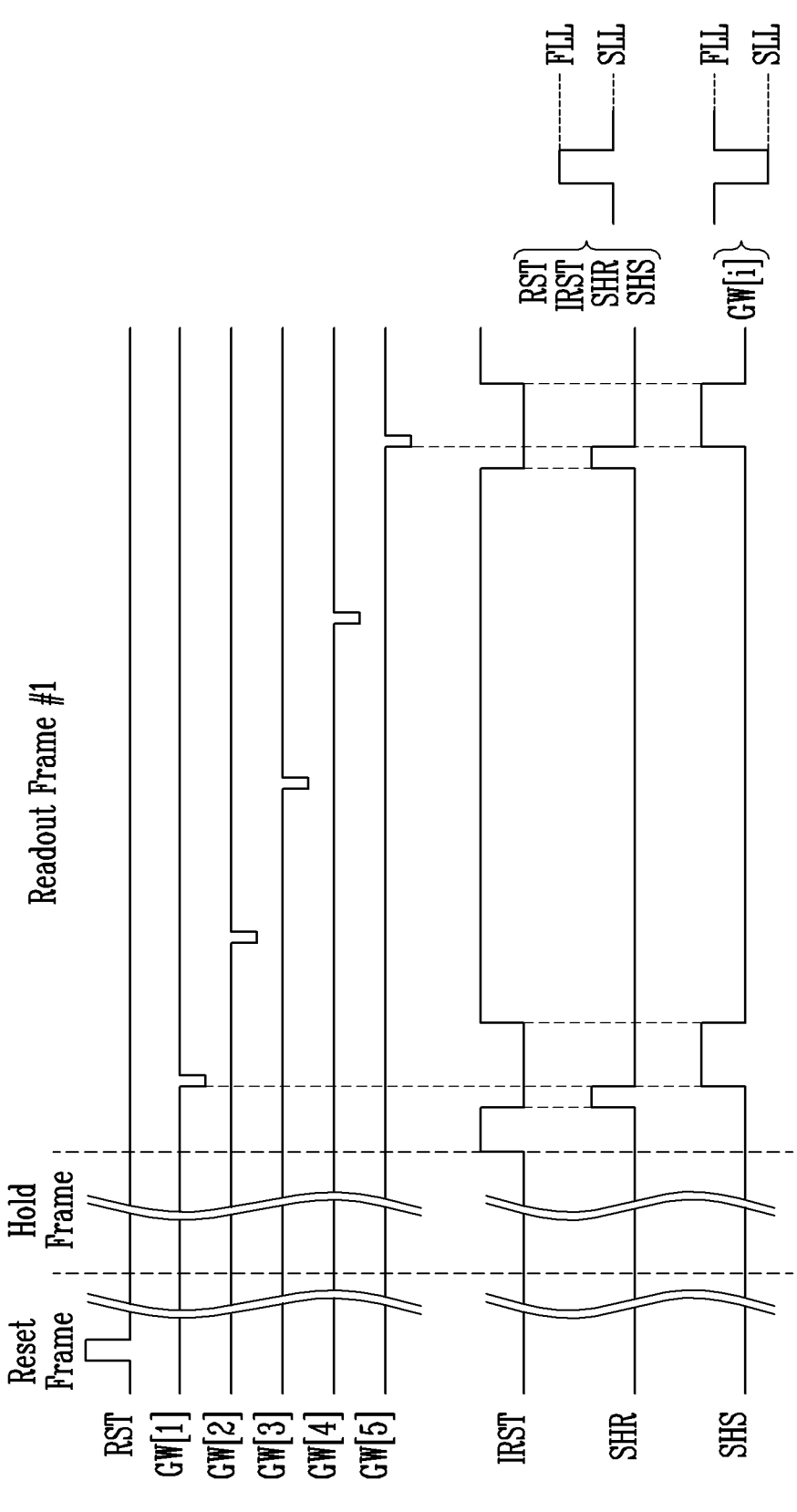
FIG. 14 illustrates another example of the first readout frame in the timing diagram illustrated in FIG. 9.

FIG. 14 illustrates another example of the first readout frame Readout Frame #1 in the timing diagram illustrated in FIG. 9.

FIG. 14 is generally similar to FIG. 13, but is different therefrom in the timing at which the voltage level of the integrator reset signal IRST makes a transition in accordance with embodiments of the present disclosure.

A timing at which the voltage level of the integrator reset signal IRST makes a transition from a turn-on level to a turn-off level may be the same as a timing at which the voltage level of the second sampling signal SHR makes a transition from a turn-off level to a turn-on level.

A timing at which the voltage level of the integrator reset signal IRST makes a transition from a turn-off level to a turn-on level may be the same as a timing at which the voltage level of the first sampling signal SHS makes a transition from a turn-on level to a turn-off level.

Figure 15:
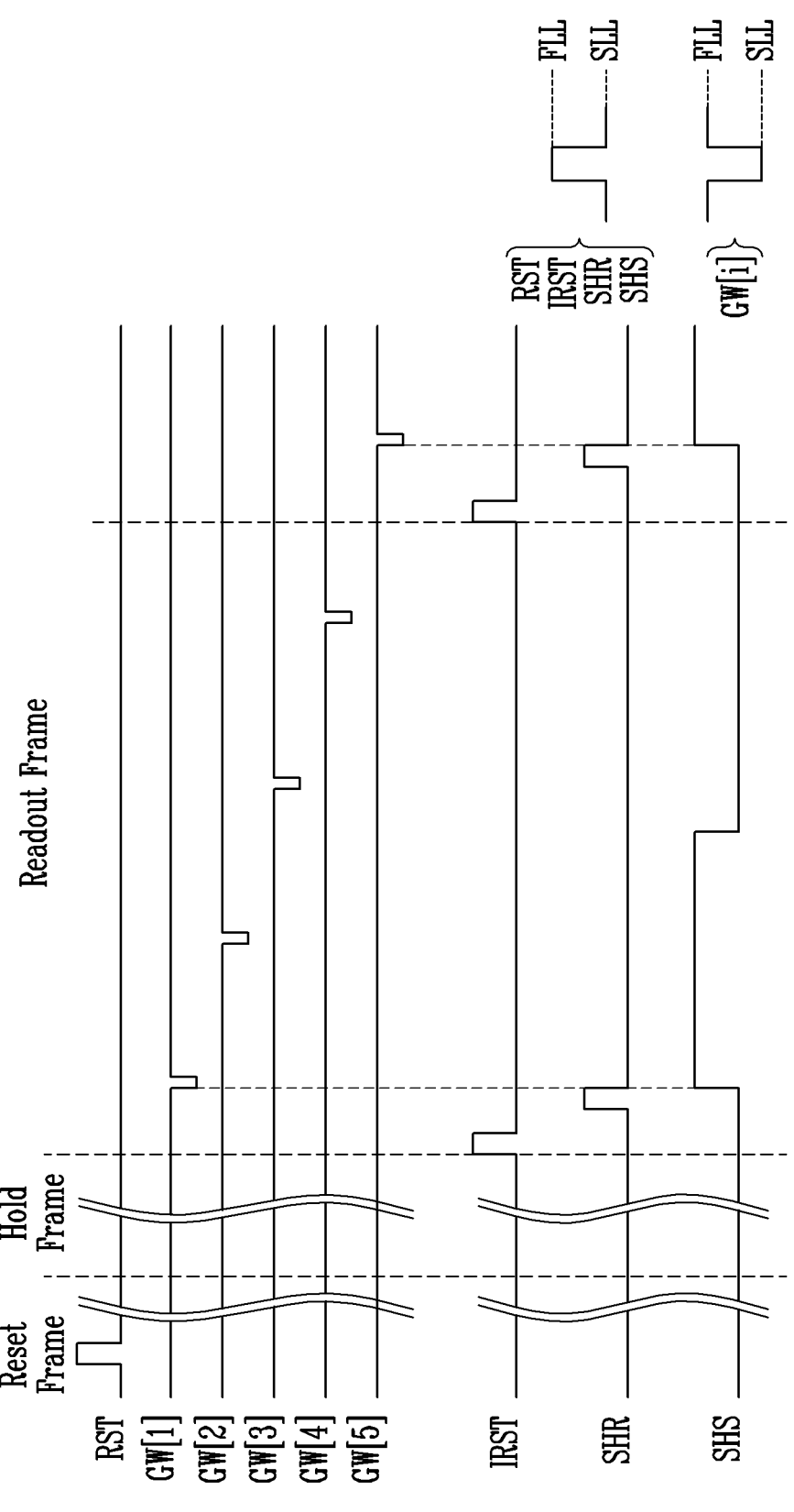
FIG. 15 illustrates an example of a readout frame in the timing diagram illustrated in FIG. 10.

FIG. 15 illustrates an example of the readout frame Readout Frame in the timing diagram illustrated in FIG. 10.

FIG. 15 illustrates only some scan signals GW[1] to GW[5] among the plurality of first scan signals GW[1] to GW[n], for convenience of explanation, in the same manner as that of FIGS. 13 and 14.

The reset frame Reset Frame and the hold frame Hold Frame have been described with reference to FIGS. 10 and 13; therefore further explanation thereof will be omitted.

In the readout frame, the reset signal RST may have a turn-off level. In the readout frame, the plurality of first scan signals GW[1] to GW[5] may sequentially (or non-sequentially) have a turn-on level.

If the readout frame starts, the integrator reset signal IRST may have a turn-on level (or the voltage level of the integrator reset signal IRST may make a transition to a turn-on level). Thereafter, the voltage level of the integrator reset signal IRST may make a transition to a turn-off level. Thereby, the feedback capacitor Cfb (refer to FIG. 12) may be reset.

After the voltage level of the integrator reset signal IRST makes a transition to a turn-off level, the voltage level of the second sampling signal SHR may make a transition from a turn-off level to a turn-on level. While the second sampling signal SHR is applied at a turn-on level, a charge corresponding to noise may be stored in the first sampling capacitor Cs1 (refer to FIG. 12). The voltage level of the second sampling signal SHR may make a transition from a turn-on level to a turn-off level.

After the voltage level of the second sampling signal SHR makes a transition to a turn-off level, the voltage level of the first sampling signal SHR may make a transition from a turn-off level to a turn-on level.

A timing at which the voltage level of the first sampling signal SHS makes a transition from a turn-off level to a turn-on level may be the same as a timing at which the voltage level of the first scan signal (e.g., GW[1]) makes a transition from a turn-off level to a turn-on level. In an embodiment, the timing at which the voltage level of the first sampling signal SHS makes a transition from a turn-off level to a turn-on level may precede (or be earlier than) the timing at which the voltage level of the first scan signal (e.g., GW[1]) makes a transition from a turn-off level to a turn-on level.

The timing at which the voltage level of the first sampling signal SHS makes a transition from a turn-off level to a turn-on level may be the same as a timing at which the voltage level of the second sampling signal SHR makes a transition from a turn-on level to a turn-off level. In an embodiment, the timing at which the voltage level of the first sampling signal SHS makes a transition from a turn-off level to a turn-on level may be later than the timing at which the voltage level of the second sampling signal SHR makes a transition from a turn-on level to a turn-off level.

The voltage level of the first sampling signal SHS may be maintained at the turn-on level at a timing at which the voltage level of a first scan signal (e.g., GW[2]) of a subsequent pixel row makes a transition from a turn-off level to a turn-on level. Thereby, two sequential pixel rows in accordance with embodiments of the present disclosure may be integrally sensed.

Referring to FIG. 15, the voltage level of the first sampling signal SHS may make a transition from a turn-on level to a turn-off level before the voltage level of a first scan signal (e.g., GW[3]) of a subsequent pixel row makes a transition from a turn-off level to a turn-on level.

A value corresponding to (or acquired by amplifying) a difference between a value sensed during a period in which the first sampling signal SHS has a turn-on level and a value sensed during a period in which the second sampling signal SHR has a turn-on level may be inputted to the analog-to-digital converter (ADC) 352 (refer to FIGS. 3 and 12).

After the voltage level of the first sampling signal SHS makes a transition from a turn-on level to a turn-off level, the voltage level of the integrator reset signal IRST may make a transition from a turn-off level to a turn-on level. A voltage level change process of each of the second sampling signal SHR and the first sampling signal SHS is as described above.

Embodiments of the present disclosure are not limited to the above description, and three or more sequential pixel rows may be integrally sensed, or non-sequential pixel rows may be integrally sensed.

For example, a timing at which the voltage level of the first sampling signal SHS makes a transition from a turn-on level to a turn-off level may be controlled so that two sequential pixel rows may be integrally sensed, or three sequential pixel rows may be integrally sensed.

For example, non-sequential pixel rows may be integrally sensed by controlling a timing at which the voltage level of the first sampling signal SHS from a turn-off level to a turn-on level. For instance, in embodiments of the present disclosure, the first pixel row (e.g., a photo sensor located on the first pixel row) and the third pixel row (e.g., a photo sensor located on the third pixel row) may be integrally sensed, or the second pixel row (e.g., a photo sensor located on the second pixel row) and the fourth pixel row (e.g., a photo sensor located on the fourth pixel row) may be integrally sensed.

For convenience of explanation, FIG. 15 illustrates an embodiment in which two sequential pixel rows (in detail, the first pixel row and the second pixel row) are integrally sensed, and embodiments of the present disclosure are not limited thereto.

Figure 16:
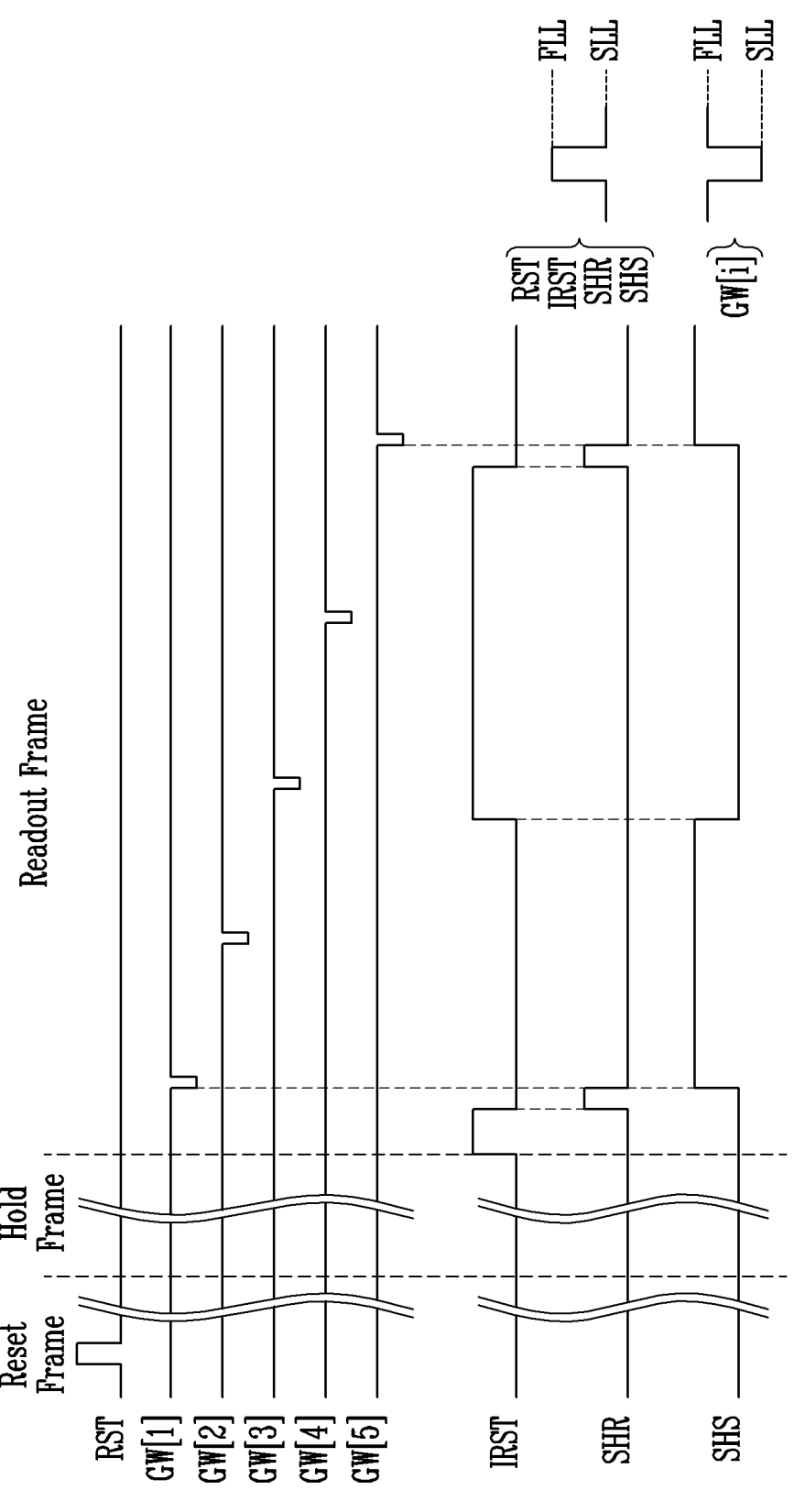
FIG. 16 illustrates another example of the readout frame in the timing diagram illustrated in FIG. 10.

FIG. 16 illustrates another example of the readout frame in the timing diagram illustrated in FIG. 10.

FIG. 16 is generally similar to FIG. 15, but is different therefrom in the timing at which the voltage level of the integrator reset signal IRST makes a transition in accordance with embodiments of the present disclosure.

A timing at which the voltage level of the integrator reset signal IRST makes a transition from a turn-on level to a turn-off level may be the same as a timing at which the voltage level of the second sampling signal SHR makes a transition from a turn-off level to a turn-on level.

A timing at which the voltage level of the integrator reset signal IRST makes a transition from a turn-off level to a turn-on level may be the same as a timing at which the voltage level of the first sampling signal SHS makes a transition from a turn-on level to a turn-off level.

Figure 17:
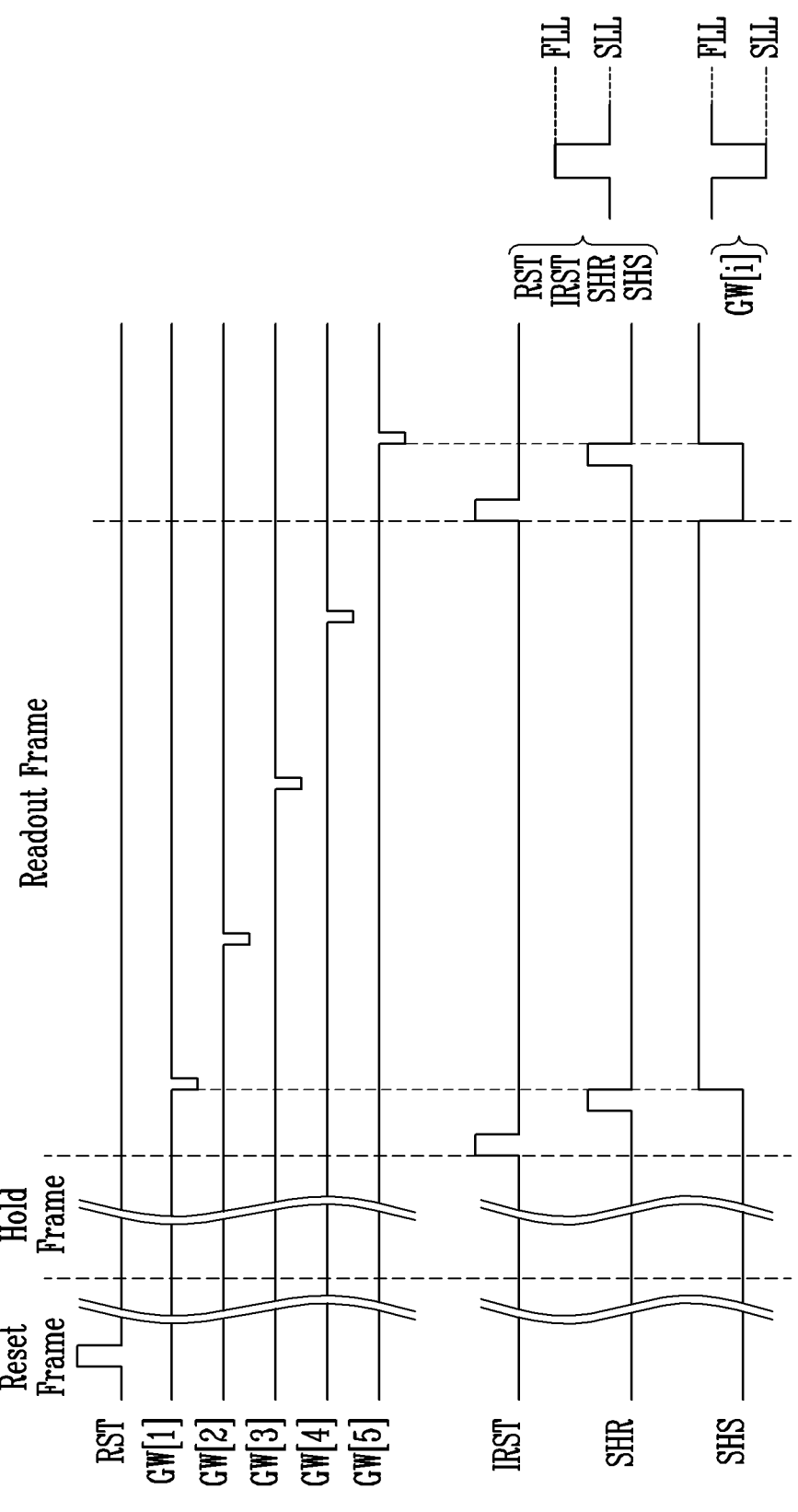
FIG. 17 illustrates an example of a readout frame in the timing diagram illustrated in FIG. 11.

FIG. 17 illustrates an example of the readout frame in the timing diagram illustrated in FIG. 11.

FIG. 17 illustrates only some scan signals GW[1] to GW[5] among the plurality of first scan signals GW[1] to GW[n], for convenience of explanation, in the same manner as that of FIGS. 13 and 16 described above.

The reset frame (Reset Frame) and the hold frame (Hold Frame) have been described with reference to FIGS. 10 and 13; therefore further explanation thereof will be omitted.

In the readout frame, the reset signal RST may have a turn-off level. In the readout frame, the plurality of first scan signals GW[1] to GW[5] may sequentially (or non-sequentially) have a turn-on level.

If the readout frame starts, the integrator reset signal IRST may have a turn-on level (or the voltage level of the integrator reset signal IRST may make a transition to a turn-on level). Thereafter, the voltage level of the integrator reset signal IRST may make a transition to a turn-off level. Thereby, the feedback capacitor Cfb (refer to FIG. 12) may be reset.

After the voltage level of the integrator reset signal IRST makes a transition to a turn-off level, the voltage level of the second sampling signal SHR may make a transition from a turn-off level to a turn-on level. While the second sampling signal SHR is applied at a turn-on level, a charge corresponding to noise may be stored in the first sampling capacitor Cs1 (refer to FIG. 12). The voltage level of the second sampling signal SHR may make a transition from a turn-on level to a turn-off level.

After the voltage level of the second sampling signal SHR makes a transition to a turn-off level, the voltage level of the first sampling signal SHR may make a transition from a turn-off level to a turn-on level.

A timing at which the voltage level of the first sampling signal SHS makes a transition from a turn-off level to a turn-on level may be the same as a timing at which the voltage level of the first scan signal (e.g., GW[1]) makes a transition from a turn-off level to a turn-on level. In an embodiment, the timing at which the voltage level of the first sampling signal SHS makes a transition from a turn-off level to a turn-on level may precede (or be earlier than) the timing at which the voltage level of the first scan signal (e.g., GW[1]) makes a transition from a turn-off level to a turn-on level.

Depending on the embodiment, the timing at which the voltage level of the first sampling signal SHS makes a transition from a turn-off level to a turn-on level may be the same as, or later than, a timing at which the voltage level of the second sampling signal SHR makes a transition from a turn-on level to a turn-off level.

The voltage level of the first sampling signal SHS may be maintained at the turn-on level until a timing at which the voltage level of a first scan signal (e.g., GW[4]) of the fourth pixel row makes a transition from a turn-off level to a turn-on level. Thereby, four successive pixel rows in accordance with embodiments of the present disclosure may be integrally sensed.

Referring to FIG. 17, the voltage level of the first sampling signal SHS may make a transition from a turn-on level to a turn-off level before the voltage level of a first scan signal (e.g., GW[5]) of a subsequent pixel row makes a transition from a turn-off level to a turn-on level.

A timing at which the voltage level of the first sampling signal SHS makes a transition from a turn-off level to a turn-on level may be the same as a timing at which the voltage level of the first scan signal (e.g., GW[5]) of the subsequent pixel row makes a transition from a turn-off level to a turn-on level.

A value corresponding to (or acquired by amplifying) a difference between a value sensed during a period in which the first sampling signal SHS has a turn-on level and a value sensed during a period in which the second sampling signal SHR has a turn-on level may be inputted to the analog-to-digital converter (ADC) 352 (refer to FIGS. 3 and 12).

After the voltage level of the first sampling signal SHS makes a transition from a turn-on level to a turn-off level, the voltage level of the integrator reset signal IRST may make a transition from a turn-off level to a turn-on level. A voltage level change process of each of the second sampling signal SHR and the first sampling signal SHS is as described above.

Figure 18:
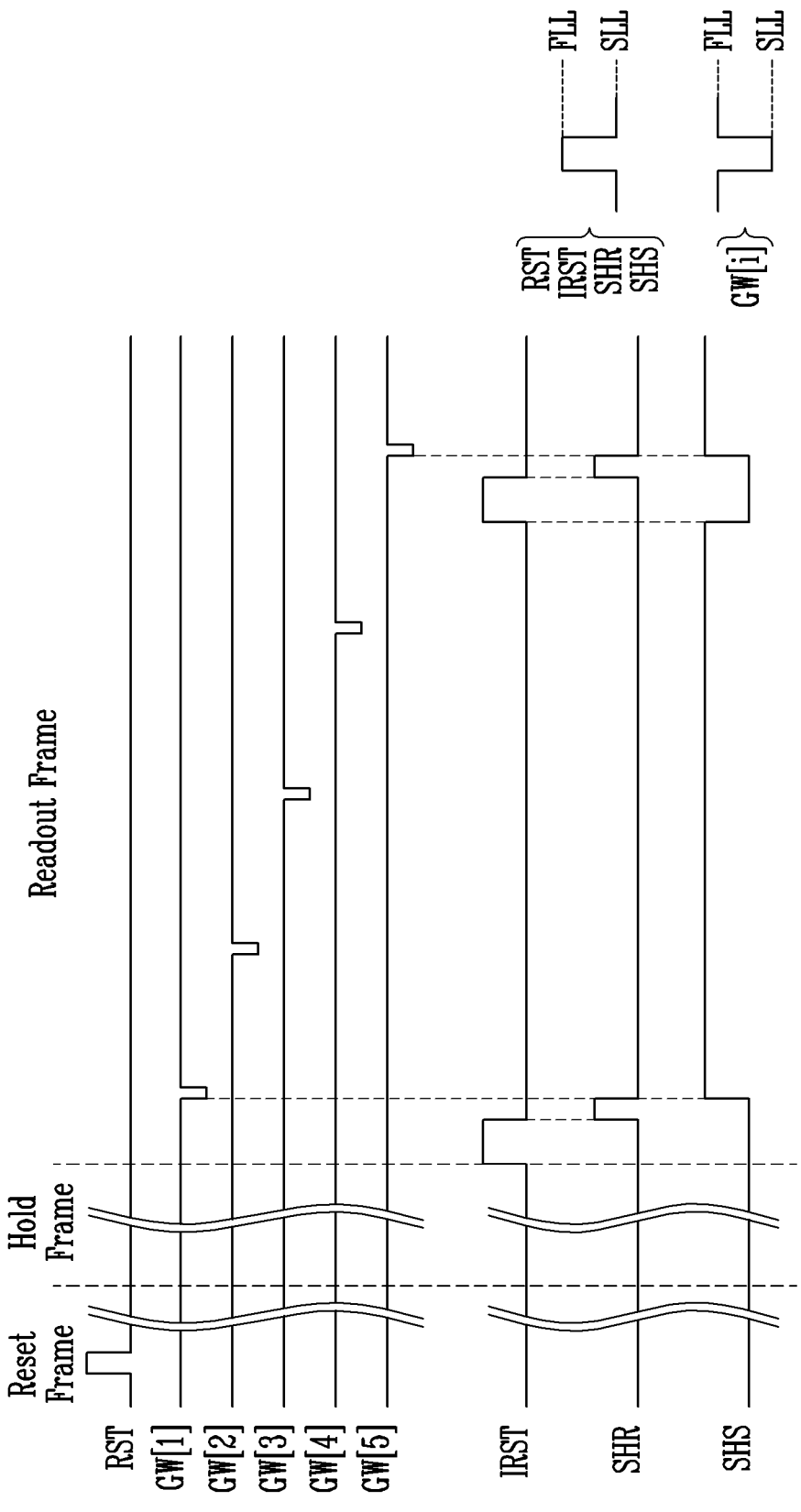
FIG. 18 illustrates another example of the readout frame in the timing diagram illustrated in FIG. 11.

FIG. 18 illustrates another example of the readout frame in the timing diagram illustrated in FIG. 11.

FIG. 18 is generally similar to FIG. 17, and is different therefrom only in the timing at which the voltage level of the integrator reset signal IRST makes a transition in accordance with embodiments of the present disclosure.

A timing at which the voltage level of the integrator reset signal IRST makes a transition from a turn-on level to a turn-off level may be the same as a timing at which the voltage level of the second sampling signal SHR makes a transition from a turn-off level to a turn-on level.

A timing at which the voltage level of the integrator reset signal IRST makes a transition from a turn-off level to a turn-on level may be the same as a timing at which the voltage level of the first sampling signal SHS makes a transition from a turn-on level to a turn-off level.

Referring to FIGS. 10 to 18, in embodiments of the present disclosure, a plurality of photo sensors may be sensed at a sensing resolution which may be differ depending on a mode selected among the first mode MODE 1 and the second mode MODE 2. For example, the sensing resolution in the second mode MODE 2 may be approximately ¼ of the sensing resolution in the first mode MODE 1. In other embodiments, the ratio of the sensing resolution difference is set based upon the particular applications for imaging analysis of target objects.

FIG. 19 is a diagram illustrating that the first area AREA 1 includes an emitting-sensing area ESA in the case where the first mode MODE 1 is selected, in accordance with embodiments of the present disclosure. It is noted here that in the following discussion of FIGS. 19-23, pixels described to be "OFF" or "black" may be pixels controlled to not emit light, e.g., via a suitable data voltage representing black data applied thereto.

Referring to FIG. 19, in the case of the selected first mode MODE 1, the first area AREA 1 for biometric authentication may be defined in the display area AA.

In embodiments of the present disclosure, the first area AREA 1 may be a preset area, or may be an area which is adaptively set by the processor 130 (shown in FIG. 1) according to the touch input from the user.

The first area AREA 1 may be set in at least a partial area of the display area AA. For example, the surface area of the first area AREA 1 may be the same as that of the display area AA in some embodiments. The surface area of the first area AREA 1 may be less than that of the display area AA in other embodiments.

The first area AREA 1 may be set to have a rectangular shape (herein, "rectangular" encompasses "square"), as illustrated in FIG. 19, but AREA 1 may alternatively be circular, oval, etc.

The first area AREA 1 may include one or more pixels and one or more photo sensors (e.g., tens, hundreds or thousands of each of pixels and photo sensors for a wearable or smart phone electronic device). In the selected first mode MODE 1, the pixels located in the first area AREA 1 may emit light, e.g., in the red wavelength band. In the selected first mode MODE 1, signals from the photo sensors located in the first area AREA 1 may be sensed. The first area AREA 1 may be defined as an emitting-sensing area ESA.

In an embodiment, in the selected first mode MODE 1, some or all of the pixels located outside the first area AREA 1 may be OFF and not emit light (at least during a time period of a finger authentication measurement). In an embodiment, in the selected first mode MODE 1, pixels located outside the first area AREA 1 may together display an image (e.g., a text image such as "put your finger on the device for fingerprint authentication") related to the biometric authentication (but not for providing light for reflection).

In an embodiment, in the selected first mode MODE 1, signals from one or more photo sensors located outside the first area AREA 1 may not be sensed. In an embodiment, in the selected first mode MODE 1, a value obtained by sensing signals from one or more photo sensors that are located outside the first area AREA 1 may not be analog-digital converted.

Figure 20:
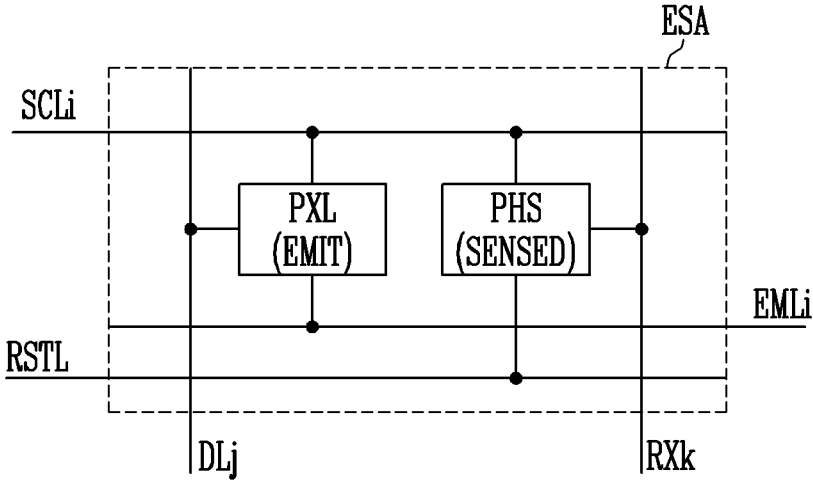
FIG. 20 is a diagram conceptually illustrating the emitting-sensing area.

FIG. 20 is a diagram conceptually illustrating the emitting-sensing area ESA.

The emitting-sensing area ESA may include pixels PXL and photo sensors PHS. For convenience of explanation, FIG. 20 illustrates one pixel PXL and one photo sensor PHS by way of example. Pixels PXL located in the emitting-sensing area ESA may emit light. Signals from photo sensors PHS located in the emitting-sensing area ESA may be sensed.

Referring to FIGS. 2 and 20 together, the processor 130 may output first image data DATA1 and a control signal CS to cause the pixels PXL located in the set emitting-sensing area ESA to emit light. The processor 130 may output a control signal CS to sense signals of photo sensors PHS located in the set emitting-sensing area ESA.

The above technique just described in connection with MODE 1, in which AREA 1 is set up for both controlling pixels therein to emit light to be reflected from an object, and for sensing signals from photo sensors within AREA 1 to image the object, may be similarly applicable to the imaging of MODE 2. However, accuracy of measurements in MODE 2 may be improved by reducing transmissive light from pixels (as opposed to reflective light from the object) incident upon the photo sensors, using the techniques described below in connection with FIGS. 21-23.

Figure 21:
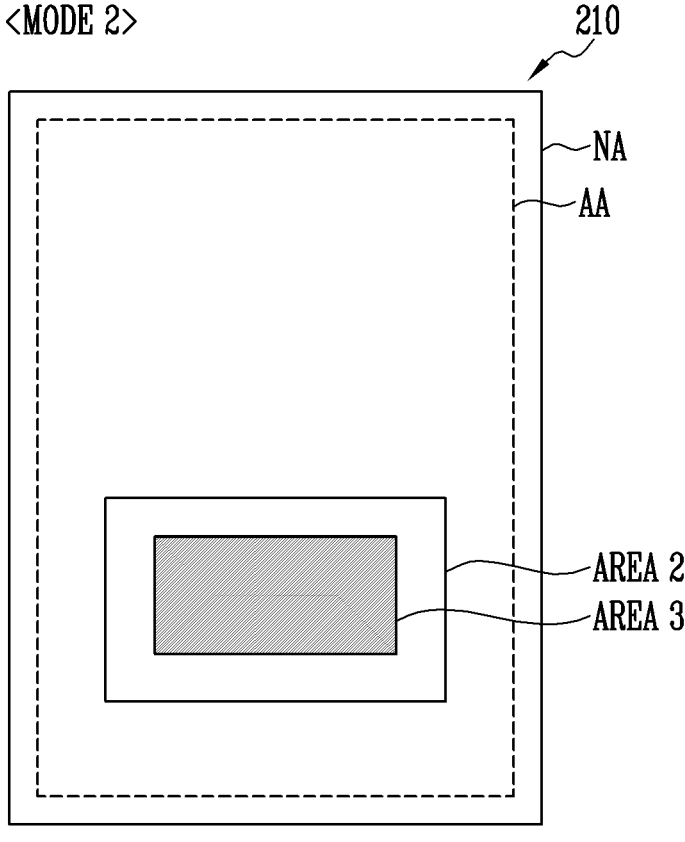
FIG. 21 is a diagram illustrating a second area and a third area in the case where the second mode is selected, in accordance with embodiments of the present disclosure.

FIG. 21 is a diagram illustrating a second area AREA 2 and a third area AREA 3 in the case where the second mode MODE 2 is selected, in accordance with embodiments of the present disclosure.

Referring to FIG. 21,21, in the case where the second mode MODE 2 is selected (or in the selected second mode MODE 2), one area for measuring a biometric signal may be defined in the display area AA. In the case where the second mode MODE 2 is selected (or in the selected second mode MODE 2), an additional area for emitting light (e.g., light for generating reflective light) may be defined in the display area AA.

The one area may be either the second area AREA 2 or the third area AREA 3. The additional area may be the other one of the second area AREA 2 and the third area AREA 3.

The second area AREA 2 may include a peripheral area (e.g., an edge area) of the third area AREA 3. The second area AREA 2 may enclose the third area AREA 3, but is not limited thereto.

In embodiments of the present disclosure, the second area AREA 2 may be a preset area, and may be an area which is adaptively set by the processor 130 (refer to FIG. 1) according to the touch input from the user.

In embodiments of the present disclosure, the third area AREA 3 may be a preset area, and may be an area which is adaptively set by the processor 130 (refer to FIG. 1) according to the touch input from the user.

In an embodiment, the second area AREA 2 may be adaptively set depending on a position at which the third area AREA 3 is set in the display area AA.

The second area AREA 2 may be set in at least a partial area of the display area AA. The second area AREA 2 may be set to have a ring shape, such as a rectangular ring shape as illustrated in FIG. 21, or a circular ring shape, that may at least partially surround the third area AREA 3.

The third area AREA 3 may be set in at least a partial area of the display area AA. The third area AREA 3 may be set to have a rectangular shape, as illustrated in FIG. 21, or a circular shape, but it is not limited thereto.

In embodiments of the present disclosure, AREA 2 and AREA 3 may be concentric areas (a center of the second area AREA 2 and a center of the third area AREA 3 may match each other (or substantially match each other)), but are not limited thereto.

In embodiments of the present disclosure, each of the second area AREA 2 and the third area AREA 3 may have a circular shape. In this case, a radius of the second area AREA 2 may be two times a radius of the third area AREA 3. For example, the radius of the third area AREA 3 may range from approximately 3 mm to approximately 4 mm (millimeter). The radius of the second area AREA 2 may range from approximately 6 mm to approximately 8 mm (millimeter). However, the above are mere examples, and may be varied by a designer in accordance with a measurement/imaging application.

The following description is made, for convenience of explanation, on the assumption that the second area AREA 2 is an area formed to measure a biometric signal and the third area AREA 3 is an area formed to emit light (e.g., light for generating reflective light). Alternatively, AREA 2 is formed to emit light and AREA 3 is formed to measure a biometric signal.

The second area AREA 2 may include one or more photo sensors. In the selected first mode MODE 2, signals from the photo sensors located in the second area AREA 2 may be sensed. The second area AREA 2 may be defined as a sensing area.

The third area AREA 3 may include one or more pixels. In the selected second mode MODE 2, the pixels that are located in the third area AREA 3 may emit light. The third area AREA 3 may be defined as a light emitting area. In an embodiment, in the selected second mode MODE 2, the one or more pixels that are located in the third area AREA 3 may emit light. The one or more pixels that emit light in the third area AREA 3 may include a pixel configured to emit light in the red wavelength band.

In an embodiment, in the selected second mode MODE 2, one or more pixels that are located outside the second area AREA 2 may not emit light. In an embodiment, in the selected second mode MODE 2, one or more pixels that are located outside the second area AREA 2 may display an image (e.g., a text image such as "put your finger on the device to measure the blood pressure (or the heart rate, the oxygen saturation, or the like)") unrelated to the biometric signal measurement.

Figure 22:
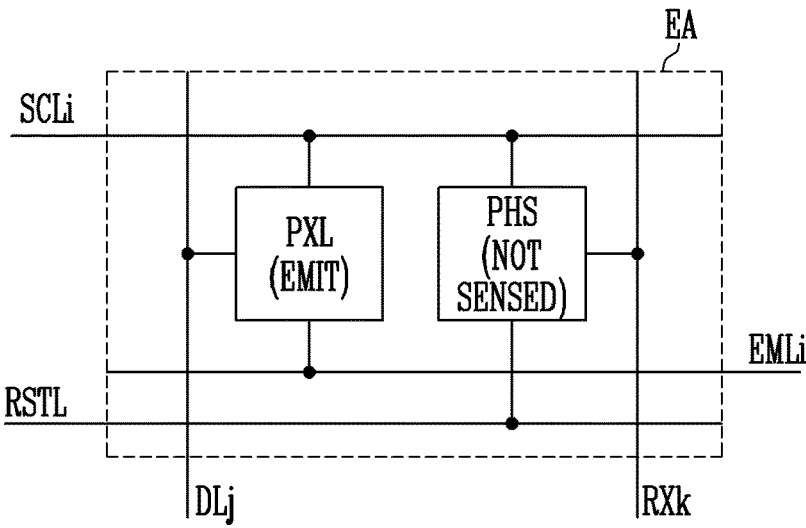
FIG. 22 is a diagram conceptually illustrating a light emitting area in accordance with embodiments of the present disclosure.

In an embodiment, in the selected second mode MODE 2, signals from one or more photo sensors located outside the second area AREA 2 may not be sensed. In an embodiment, in the selected second mode MODE 2, a value obtained by sensing signals from one or more photo sensors located outside the second area AREA 2 may not be analog-digital converted. FIG. 22 is a diagram conceptually illustrating a light emitting area EA in accordance with embodiments of the present disclosure.

Referring to FIG. 22, the light emitting area EA may include one or more pixels PXL. The pixel that is located in the light emitting area EA may emit light. The pixel PXL may include, for example, a pixel configured to emit light in the red wavelength band.

The light emitting area EA may include one or more photo-sensors PHS. Signals from the photo sensor PHS located in the light emitting area EA may not be sensed. In an embodiment, even if signals from the photo sensor PHS located in the light emitting area EA are sensed, the sensed value may not be analog-to-digital converted.

Referring to FIGS. 2 and 22 together, in embodiments of the present disclosure, the processor 130 may output first image data DATA1 and a control signal CS to allow the pixels PXL located in the set light emitting area EA to emit light. In embodiments of the present disclosure, the sensing circuit 224 may sense a photo sensor PHS located in at least a partial area of the display area AA other than the light emitting area EA.

Figure 23:
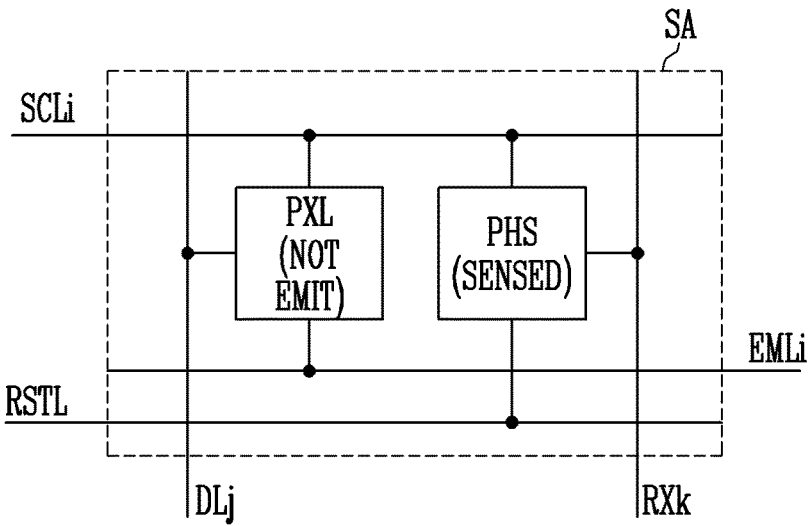
FIG. 23 is a diagram conceptually illustrating a sensing area in accordance with embodiments of the present disclosure.

FIG. 23 is a diagram conceptually illustrating a sensing area SA in accordance with embodiments of the present disclosure.

Referring to FIG. 23, the sensing area SA may include one or more photo sensors PHS. In embodiments of the present disclosure, signals from the photo sensor PHS located in the sensing area SA may be sensed. A value obtained by sensing the photo sensor PHS signal located in the sensing area SA may be analog-digital converted.

The sensing area SA may include one or more pixels PXL. The pixel PXL located in the sensing area SA may be OFF and not emit light (or may not substantially emit light). For example, a data voltage for displaying a low-grayscale image (e.g., an image of gray scale 0, or a black gray scale) may be applied, through the data line DLj, to the pixel PXL that is located in the sensing area SA.

Referring to FIGS. 2 and 23 together, the processor 130 may output a control signal CS to sense a signal of the photo sensor PHS located in the set sensing area SA. The sensing circuit 224 may sense a photo sensor PHS located in the sensing area SA. The processor 130 may output first image data DATA1 such that the pixel PXL located in the sensing area SA does not emit light (or substantially does not emit light). The first image data outputted by the processor 130 in the selected second mode may include data for displaying a black image.

Figure 24:
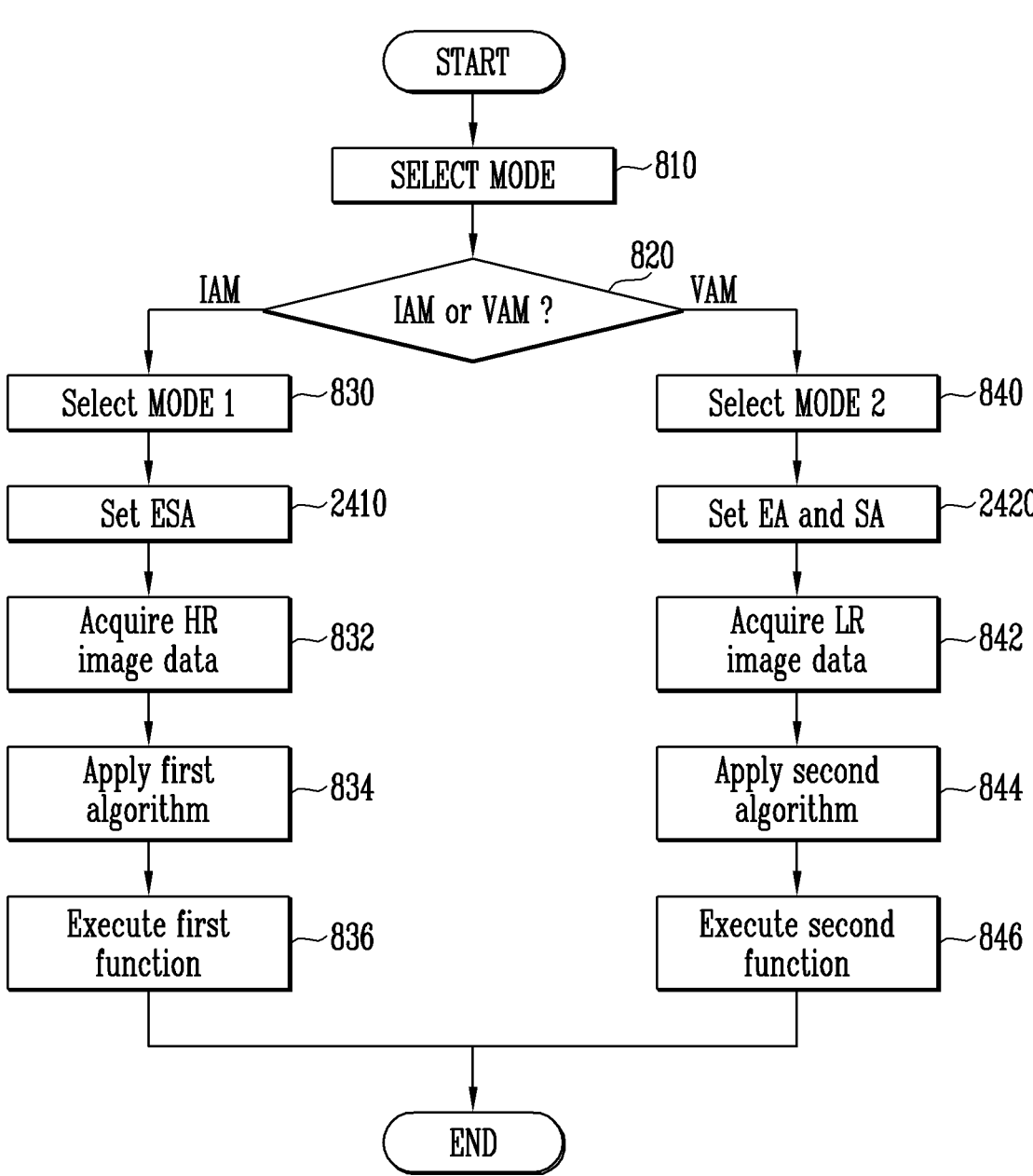
FIG. 24 is a diagram illustrating an example of the operation of setting the emitting-sensing area, and an example of the operation of setting the light emitting area and the sensing area, based on the flowchart illustrated in FIG. 8.

FIG. 24 is a diagram illustrating a flowchart that further includes operation 2410 of setting the emitting-sensing area ESA and operation 2420 of setting the light emitting area EA and the sensing area SA based on the flowchart illustrated in FIG. 8.

Referring to FIG. 24, a method of driving an electronic device in accordance with embodiments of the present disclosure may further include operation 2410 of setting the emitting-sensing area ESA. Operation 2410 of setting the emitting-sensing area ESA may be performed, for example, after operation 830 of selecting the first mode MODE 1. Operation 832 of acquiring image data having a high sensing resolution from the set emitting-sensing area ESA may be performed.

The description of the emitting-sensing area ESA is the same as that described above with reference to FIGS. 19 and 20; therefore, further explanation thereof will be omitted.

Referring to FIG. 24, the method of driving the electronic device in accordance with embodiments of the present disclosure may further include operation 2420 of setting the light emitting area EA and the sensing area SA. In an embodiment, operation 2420 of setting the light emitting area EA and the sensing area SA may be divided into the operation of setting the light emitting area EA and the operation of setting the sensing area SA. Operation 2420 of setting the light emitting area EA and the sensing area SA may be performed, for example, after operation 840 of selecting the second mode MODE 2. Operation 842 of acquiring image data having a low sensing resolution from the set sensing area SA may be performed.

The description of the light emitting area EA and the sensing area SA is the same as that described above with reference to FIGS. 21 to 23; therefore, further explanation thereof will be omitted.

Figure 25:
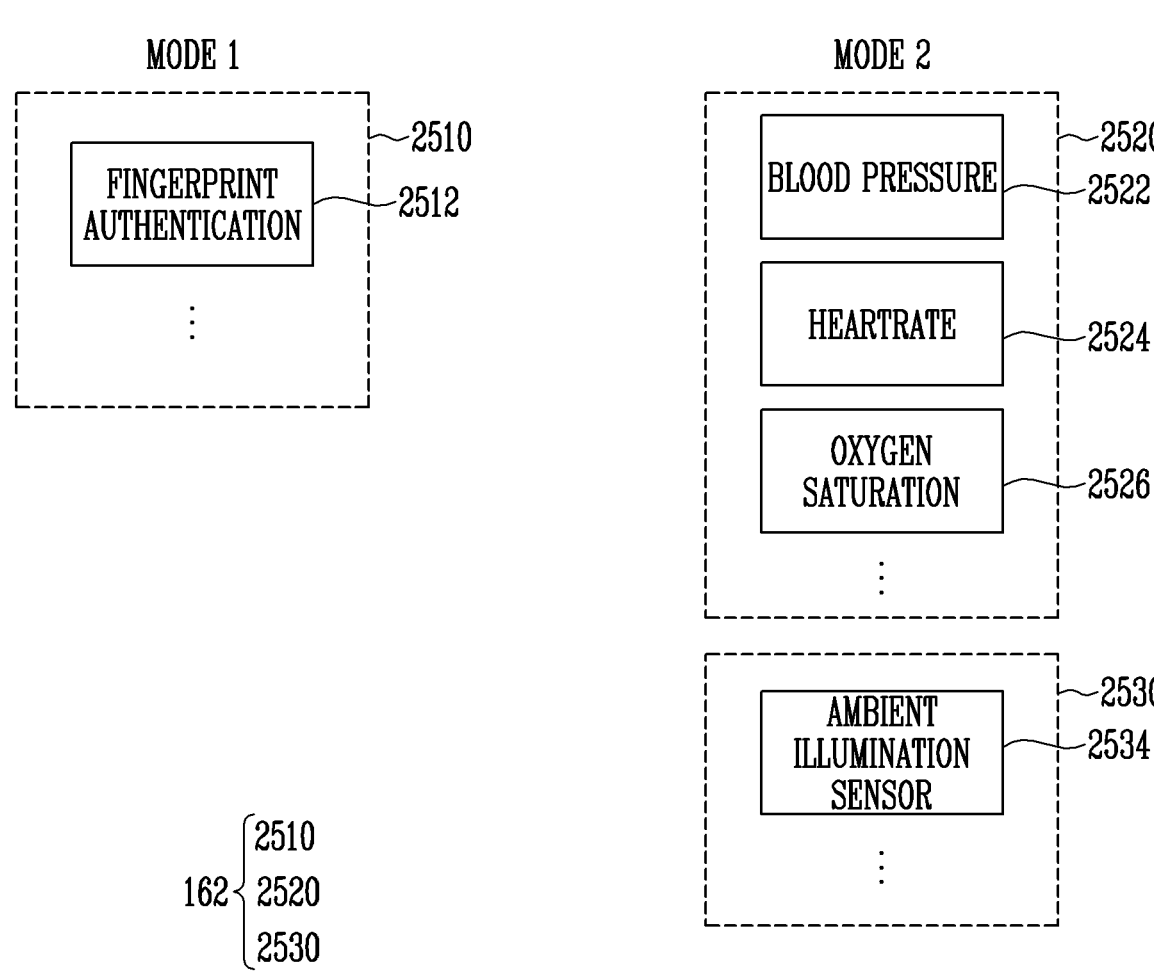
FIG. 25 is a diagram illustrating software stored in the electronic device in accordance with embodiments of the present disclosure.

FIG. 25 is a diagram illustrating software 162 stored in the electronic device in accordance with embodiments of the present disclosure.

The electronic device in accordance with embodiments of the present disclosure may include the memory 150 (refer to FIG. 1), and one or more applications 162 may be stored in the memory 150.

The applications 162 stored in the memory 150 may include, for example, biometric authentication software 2510, biometric signal measuring software 2520, illuminance measuring software 2530, and the like.

The biometric authentication software 2510 may include a fingerprint authentication module 2512 configured to perform a biometric authentication function based on an acquired fingerprint image. In an embodiment, the biometric authentication software 2510 may include a photoplethysmography (PPG) authentication module configured to perform a biometric authentication function based on the fact that the intensity of light absorbed and/or reflected varies depending on the flow of blood.

If the biometric authentication software 2510 is executed, the electronic device in accordance with embodiments of the present disclosure may select the first mode MODE 1. Hence, the electronic device may acquire an image having a high sensing resolution (e.g., the first sensing resolution).

The biometric signal measuring software 2520 may include a blood pressure measuring module 2522, a heart rate measuring module 2524, an oxygen saturation measuring module 2526, and the like. Depending on the embodiment, the biometric signal measuring software 2520 may include a PPG measuring module, a heart health measuring module (e.g., an arrhythmia inspection module, or a blood vessel elasticity inspection module), or the like.

If the biometric signal measuring software 2520 is executed, the electronic device may emit light in the red wavelength band. The electronic device may measure a biometric signal by sensing variation in the quantity of light that is emitted, reflected by an adjacent object (e.g., a blood vessel wall, a muscle, a bone, or the like around a user's finger), and then is re-incident.

If the biometric signal measuring software 2520 is executed, the electronic device in accordance with embodiments of the present disclosure may select the second mode MODE 2. Therefore, the electronic device may acquire a still image having a low sensing resolution (e.g., the second sensing resolution) and a video (moving image) having a low sensing resolution (e.g., the second sensing resolution).

The illuminance measuring software 2530 may include an illuminance sensor module 2534 configured to measure illuminance (or a variation in illuminance) of ambient light. In an embodiment, the illuminance measuring software 2530 may include a proximity sensing module configured to temporarily turn off the touch sensing function of the electronic device, using characteristics in which the light receiving amount varies as an object (e.g., a user's face or the like) comes close to the display area of the electronic device.

If the illuminance measuring software 2530 is executed, the electronic device in accordance with embodiments of the present disclosure may select the second mode MODE 2. The electronic device may measure illuminance (or a variation in illuminance) by sensing a variation in quantity of light that is incident from external lighting.

As described above, an electronic device and a method of driving the electronic device in accordance with embodiments of the present disclosure may provide a biometric authentication function and a biometric signal measuring function.

The electronic device and the method of driving the electronic device in accordance with embodiments of the present disclosure may provide a biometric authentication function and a biometric signal measuring function, with a display device having a relatively simple configuration.

In the electronic device and the method of driving the electronic device in accordance with embodiments of the present disclosure, a sensing resolution may be controlled to vary depending on a selected mode so that a biometric authentication function with a high level of security and a biometric signal measuring function having improved accuracy can be provided.

Although example embodiments of the present disclosure have been disclosed for illustrative purposes, those skilled in the art will appreciate that various modifications, additions and substitutions are possible, without departing from the scope and spirit of the present disclosure as disclosed in the accompanying claims. Accordingly, the bounds and scope of the present disclosure should be determined by the technical spirit of the following claims.

What is claimed is:

1. An electronic device comprising:
a display panel including a display area including non-overlapping second and third areas, with first photo sensors and first pixels disposed in the second area and second pixels and second photo sensors disposed in the third area;
a panel driving circuit connected to each of the second and third areas;
a sensing circuit connected to each of the second and third areas;
a memory configured to store at least one application; and
a processor configured to execute instructions read from the memory, to control the panel driving circuit and the sensing circuit so that in a video capture mode of the at least one application, the panel driving circuit causes the first pixels to emit light for generating reflective light from an object, and causes the second pixels to not emit light for generating reflective light from the object, and the sensing circuit senses signals from the second photo sensors but not from the first photo sensors to generate video data of the object based on the reflective light.

2. The electronic device according to claim 1, wherein in a still image capture mode of the at least one application, the processor controls the panel driving circuit to cause the first pixels or the second pixels to emit light for generating reflective light from an object, and controls the sensing circuit to sense signals from the first photo sensors or the second photo sensors, respectively, to generate a still image of the object based on the reflective light.

3. The electronic device according to claim 1, wherein the second area and the third area are concentric areas of a first area formed by the second area and the third area, the second area is a central region of the first area, and the third area is a peripheral area of the first area.

4. The electronic device according to claim 1, wherein the second area and the third area are concentric areas of a first area formed by the second area and the third area, the third area is a central region of the first area, and the second area is a peripheral area of the first area.

5. The electronic device according to claim 1, wherein the light emitted by the first pixels to generate reflective light is red light or infrared light.

6. An electronic device comprising:
a display device including a display panel on which a plurality of photo sensors are disposed, and a readout circuit configured to sense signals from the plurality of photo sensors; and
a processor configured to control a sensing resolution at which the readout circuit senses the signals from the plurality of photo sensors such that a first sensing resolution in a first mode for capturing image data in a first biometric-related application is different from a second sensing resolution in a second mode for capturing image data in a second biometric-related application different from the first biometric-related application,
wherein the processor is configured to acquire an image in the first mode and to acquire a video in the second mode.

7. The electronic device according to claim 6, further comprising:
a memory in which reference data is stored,
wherein the processor compares a value acquired by the readout circuit in the selected first mode with the reference data.

8. The electronic device according to claim 7,
wherein first software, and image data having a first sensing resolution and generated by executing the first software by the processor are stored in the memory, and
wherein the processor executes the first software, and compares the generated image data having the first sensing resolution with the reference data.

9. An electronic device comprising:
a display device including a display panel on which a plurality of photo sensors are disposed, and a readout circuit configured to sense signals from the plurality of photo sensors;
a processor configured to control a sensing resolution at which the readout circuit senses the signals from the plurality of photo sensors such that the sensing resolution varies depending on a mode selected from between a first mode and a second mode; and
a memory,
wherein the processor generates image data having a second sensing resolution based on a value acquired by the readout circuit in the selected second mode, and
wherein video data having the second sensing resolution and including the image data having the second sensing resolution is stored in the memory.

10. The electronic device according to claim 9,
wherein second software, and video data having the second sensing resolution and generated by executing the second software by the processor are stored in the memory, and
wherein the processor executes the second software, and generates biometric signal data of a user of the electronic device based on the generated video data having the second sensing resolution.

11. The electronic device according to claim 10, wherein the second software comprises at least one of:
blood pressure measuring circuitry configured to measure a blood pressure of the user of the electronic device based on the video data having the second sensing resolution;
heart rate measuring circuitry configured to measure a heart rate of the user of the electronic device based on the video data having the second sensing resolution; and
oxygen saturation measuring circuitry configured to measure an oxygen saturation of the user of the electronic device based on the video data having the second sensing resolution.

12. The electronic device according to claim 6,
wherein a plurality of scan lines extending in a row direction, a first pixel row including a first photo sensor and a first pixel, a second pixel row including a second photo sensor and a second pixel, and a sensing line electrically connected to the first photo sensor and the second photo sensor are disposed on the display panel,
wherein the first pixel and the first photo sensor are electrically connected to any one scan line among the plurality of scan lines, and
wherein the second pixel and the second photo sensor are electrically connected to another scan line among the plurality of scan lines.

13. The electronic device according to claim 12, wherein the processor outputs a control signal to cause the readout circuit to sense signals from each of the first photo sensor and the second photo sensor in the first mode.

14. The electronic device according to claim 12, wherein the processor outputs a control signal to cause the readout circuit to sense signals from both the first photo sensor and the second photo sensor in the second mode.

15. An electronic device comprising:
a display device including a display panel on which a plurality of photo sensors are disposed, and a readout circuit configured to sense signals from the plurality of photo sensors;
a processor configured to control a sensing resolution at which the readout circuit senses the signals from the plurality of photo sensors such that the sensing resolution varies depending on a mode selected from between a first mode and a second mode;
wherein a plurality of scan lines extending in a row direction, a first pixel row including a first photo sensor and a first pixel, a second pixel row including a second photo sensor and a second pixel, and a sensing line electrically connected to the first photo sensor and the second photo sensor are disposed on the display panel,
wherein the first pixel and the first photo sensor are electrically connected to any one scan line among the plurality of scan lines, and
wherein the second pixel and the second photo sensor are electrically connected to another scan line among the plurality of scan lines,
wherein the readout circuit includes an integrator and a sample-and-hold circuit, and
wherein the integrator comprises:
an operational amplifier including an input terminal electrically connected to the sensing line; and
a first node electrically connected to an output terminal of the operational amplifier, and
wherein the sample-and-hold circuit comprises:
a first capacitor element;
a second capacitor element;
a first switching element configured to switch electrical connection between the first node and the first capacitor element; and
a second switching element configured to switch electrical connection between the first node and the second capacitor element, and
wherein the processor controls a length of a period, during which the first switching element is turned on, such that the length of the period varies depending on a mode selected from between the first mode and the second mode.

16. The electronic device according to claim 15, wherein the processor outputs a control signal for turning on the second switching element in at least a portion of a period during which the first switching element is not turned on.

17. An electronic device comprising:
a display device including a display panel on which a plurality of photo sensors are disposed, and a readout circuit configured to sense signals from the plurality of photo sensors;
a processor configured to control a sensing resolution at which the readout circuit senses the signals from the plurality of photo sensors such that the sensing resolution varies depending on a mode selected from between a first mode and a second mode;
wherein a plurality of scan lines extending in a row direction, a first pixel row including a first photo sensor and a first pixel, a second pixel row including a second photo sensor and a second pixel, and a sensing line electrically connected to the first photo sensor and the second photo sensor are disposed on the display panel,
wherein the first pixel and the first photo sensor are electrically connected to any one scan line among the plurality of scan lines, and
wherein the second pixel and the second photo sensor are electrically connected to another scan line among the plurality of scan lines,
wherein the display panel includes a display area in which a plurality of pixels including the first pixel and the second pixel and a plurality of photo sensors including the first photo sensor and the second photo sensor are disposed,
wherein the display area includes a first area in which first pixels among the plurality of pixels and first photo sensors among the plurality of photo sensors are located,
wherein the display area further includes a second area located within a perimeter of the first area,
wherein at least one pixel among remaining pixels and at least one photo sensor among remaining photo sensors are located in the second area,
wherein the processor, according to the selected second mode:
outputs image data to cause a pixel located in any one of the first area and the second area to emit light, and
outputs a control signal to sense signals from a photo sensor located in a remaining one of the first area and the second area.

18. The electronic device according to claim 17, wherein the processor, according to the selected first mode, outputs image data to cause at least one of the first pixels located in the first area to emit light, and outputs a control signal to sense signals from at least one of the first photo sensors located in the first area.

19. A method of driving an electronic device including a processor and a display device configured to be controlled by the processor, the display device including a plurality of photo sensors and a readout circuit configured to sense signals from the plurality of photo sensors,
the method comprising:
selecting a mode among a first mode and a second mode; and
sensing, by the readout circuit, the signals from the plurality of photo sensors at a sensing resolution varying depending on the selected mode,
wherein a first photo sensor and a second photo sensor of the plurality of photo sensors are respectively disposed in different pixel rows in the display device, and the readout circuit includes a capacitor element,
the method further comprising:
storing a value acquired by sensing the first photo sensor in the selected first mode in the capacitor element;
converting an analog voltage value including the value acquired by sensing the first photo sensor to a digital value, and outputting the digital value;
storing a value acquired by sensing a signal from the second photo sensor in the selected first mode in the capacitor element; and
converting an analog voltage value including the value acquired by sensing the signal from the second photo sensor to a digital value, and outputting the digital value.

20. The method according to claim 19, wherein the electronic device further comprises a memory, the method further comprising:

executing first software stored in the memory according to the selected first mode;

generating image data having a first sensing resolution according to the executed first software; and comparing the image data having the first sensing resolution with reference data prestored in the memory.

21. The method according to claim 19, wherein the electronic device further comprises a memory, the method further comprising:

executing second software stored in the memory according to the selected second mode;

generating a plurality of pieces of image data having a second sensing resolution according to the executed second software; and generating biometric signal data of a user of the electronic device, based on video data having the second sensing resolution and including the plurality of pieces of generated image data having the second sensing resolution.

22. The method according to claim 19, wherein the display device includes a first area including any one of the plurality of photo sensors and at least one pixel, the method further comprising:

outputting, by the processor, image data to allow the at least one pixel to emit light in the selected first mode; and outputting, by the processor, a control signal to sense a signal from the any one photo sensor in the selected first mode.

23. The method according to claim 19, wherein the display device includes a second area and a third area located around a peripheral area of the second area, wherein each of the second area and the third area includes any one of the plurality of photo sensors, and wherein each of the second area and the third area includes at least one pixel, the method further comprising:

outputting, by the processor, image data to cause the at least one pixel in any one of the second area and the third area to emit light in the selected second mode; and outputting, by the processor, a control signal to sense a signal of the photo sensor in a remaining one of the second area and the third area in the selected second mode.

24. A method of driving an electronic device including a processor and a display device configured to be controlled by the processor, the display device including a plurality of photo sensors and a readout circuit configured to sense signals from the plurality of photo sensors, the method comprising:

selecting a mode among a first mode and a second mode; and sensing, by the readout circuit, the signals from the plurality of photo sensors at a sensing resolution varying depending on the selected mode, wherein a first photo sensor and a second photo sensor of the plurality of photo sensors are respectively disposed in different pixel rows in the display device, the method further comprising:

storing a value acquired by sensing a signal from the first photo sensor in the selected second mode in a capacitor element;

storing a value acquired by sensing the second photo sensor in the selected second mode in the capacitor element; and converting an analog voltage value including the value acquired by sensing the first photo sensor and the value acquired by sensing the second photo sensor to a digital value, and outputting the digital value.

* * * * *